US007371851B1

(12) United States Patent
Lexow

(10) Patent No.: US 7,371,851 B1
(45) Date of Patent: May 13, 2008

(54) METHODS OF CLONING AND PRODUCING FRAGMENT CHAINS WITH READABLE INFORMATION CONTENT

(75) Inventor: Preben Lexow, Husoysund (NO)

(73) Assignee: Complete Genomics AS, Oslo (NO)

( * ) Notice: Subject to any disclaimer, the term of this patent is extended or adjusted under 35 U.S.C. 154(b) by 848 days.

(21) Appl. No.: 10/019,258

(22) PCT Filed: Jun. 27, 2000

(86) PCT No.: PCT/GB00/02512

§ 371 (c)(1), (2), (4) Date: Sep. 23, 2002

(87) PCT Pub. No.: WO01/00816

PCT Pub. Date: Jan. 4, 2001

(30) Foreign Application Priority Data

| | | |
|---|---|---|
| Jun. 28, 1999 | (NO) | 19991325 |
| Jun. 20, 2000 | (NO) | 20003190 |
| Jun. 20, 2000 | (NO) | 20003191 |

(51) Int. Cl.

| | |
|---|---|
| ***C07H 21/00*** | (2006.01) |
| ***C07H 21/02*** | (2006.01) |
| ***C07H 21/04*** | (2006.01) |
| ***C12Q 1/68*** | (2006.01) |

(52) U.S. Cl. ........................ 536/25.3; 435/6; 536/23.1; 536/24.3

(58) Field of Classification Search .................... 435/6; 536/25.3, 23.1, 24.3
See application file for complete search history.

(56) References Cited

U.S. PATENT DOCUMENTS

| | | | | |
|---|---|---|---|---|
| 5,976,846 | A * | 11/1999 | Passmore et al. | 435/483 |
| 6,030,657 | A * | 2/2000 | Butland et al. | 427/7 |
| 6,183,966 | B1 * | 2/2001 | Gray et al. | 435/6 |
| 6,312,911 | B1 * | 11/2001 | Bancroft et al. | 435/6 |
| 6,613,514 | B2 * | 9/2003 | Patten et al. | 435/6 |

FOREIGN PATENT DOCUMENTS

| | | | |
|---|---|---|---|
| DE | 196 33 427 | A1 | 3/1998 |
| EP | 0 245 130 | A1 | 11/1987 |
| WO | WO 94/01582 | A1 | 1/1994 |
| WO | WO 98/14619 | A1 | 4/1998 |
| WO | WO98/38326 | * | 9/1998 |
| WO | WO 98/38326 | A1 | 9/1998 |
| WO | WO 00/39333 | A1 | 7/2000 |

OTHER PUBLICATIONS

Saiki et al., Nature 324: 163-166 (1986).*

The Stratagene Catalog, Gene Characterization Kits p. 39 (1988).*

Tyagi et al. Multicolor Molecular beacons for allele discrimination. Nature Biotechnology 16 : 49-53 (Jan. 1998).*

Rothstein et al., Synthetic adaptors for Cloning DNA. Methods in Enzymology 68 : 98-109 (1979).*

Gene Characterization Kits ; The Stratagene Catalog p. 39 (1988).*

Brake, A. J. et al., "Alpha-Factor-Directed Synthesis and Secretion of Mature Foreign Proteins in *Saccharomyces-cerevisiae,*" *Proceedings of the National Academy of Sciences*, Aug. 1984, pp. 4642-4646, vol. 81, No. 15. USA.

Korobko V., et al., "Oligo Nucleotide Adaptors Cleavable by Restriction Nuclease HGA-1 and Their Application for DNA Synthesis," *Bioorganicheskay Khimiya*, 1982, pp. 830-839, vol. 8. Abstract from Biosciences Information Service, Philadelphia, PA, 1982.

Lebedenko, E.N., et al., "Method of Artificial DNA Splicing by Directed Ligation (SDL)," *Nucleic Acids Research*, 1991, pp. 6757-6761, vol 19, No. 24. Oxford University Press, U.K.

Mahadeva, Harin et al., "A simple and efficient method for the isolation of differentially expressed genes," *Journal of Molecular Biology*, Dec. 18, 1998, pp. 1391-1398, vol. 284, No. 5.

Mandecki W, et al., "*FOK*-I Method of Gene Synthesis," *Gene*, 1988, pp. 101-107, vol. 68, No. 1, Elsevier Science Publishers B.V., The Netherlands.

Padgett, Kerstien et al., "Creating seamless junctions independent of restriction sites in PCR cloning," *Gene*, 1996, pp. 31-35, vol. 168, No. 1, Elsevier Science B.V., The Netherlands.

Szybalski, W,. et al., "Class-IIs Restriction Enzymes—a Review," *Gene*, 1991, pp. 13-26, vol. 100. Elsevier Science Publishers B.V., The Netherlands.

Unrau, Paul, et al., "Non-cloning amplification of specific DNA fragments from whole genomic DNA digets using DNA 'indexers'," *GENE*, 1994, pp. 163-169, vol. 145, No. 2. Elsevier Science Publishers B.V., The Netherlands.

Vermersch, P., et al., "The Use of a Selectable FOKI Cassette in DNA Replacement Mutagenesis of the R388 Dihydrofolate Reductase Gene," *Gene*, 1987, pp. 229-238, vol. 54, No. 2-3. Elsevier Science Publishers B.V., The Netherlands.

* cited by examiner

*Primary Examiner*—Ethan Whisenant
(74) *Attorney, Agent, or Firm*—Rothwell, Figg, Ernst & Manbeck

(57) ABSTRACT

The present invention provides a method of attaching a fragment of a first nucleic acid molecule to a second nucleic acid molecule using adapters to mediate the binding particularly in methods of cloning, methods of producing fragment chains with a readily readable information content, particularly comprising fragments corresponding to code, such as alphanumeric code, the nucleic acid molecules thus produced and kits for performing such methods.

4 Claims, 6 Drawing Sheets

Figure 1:
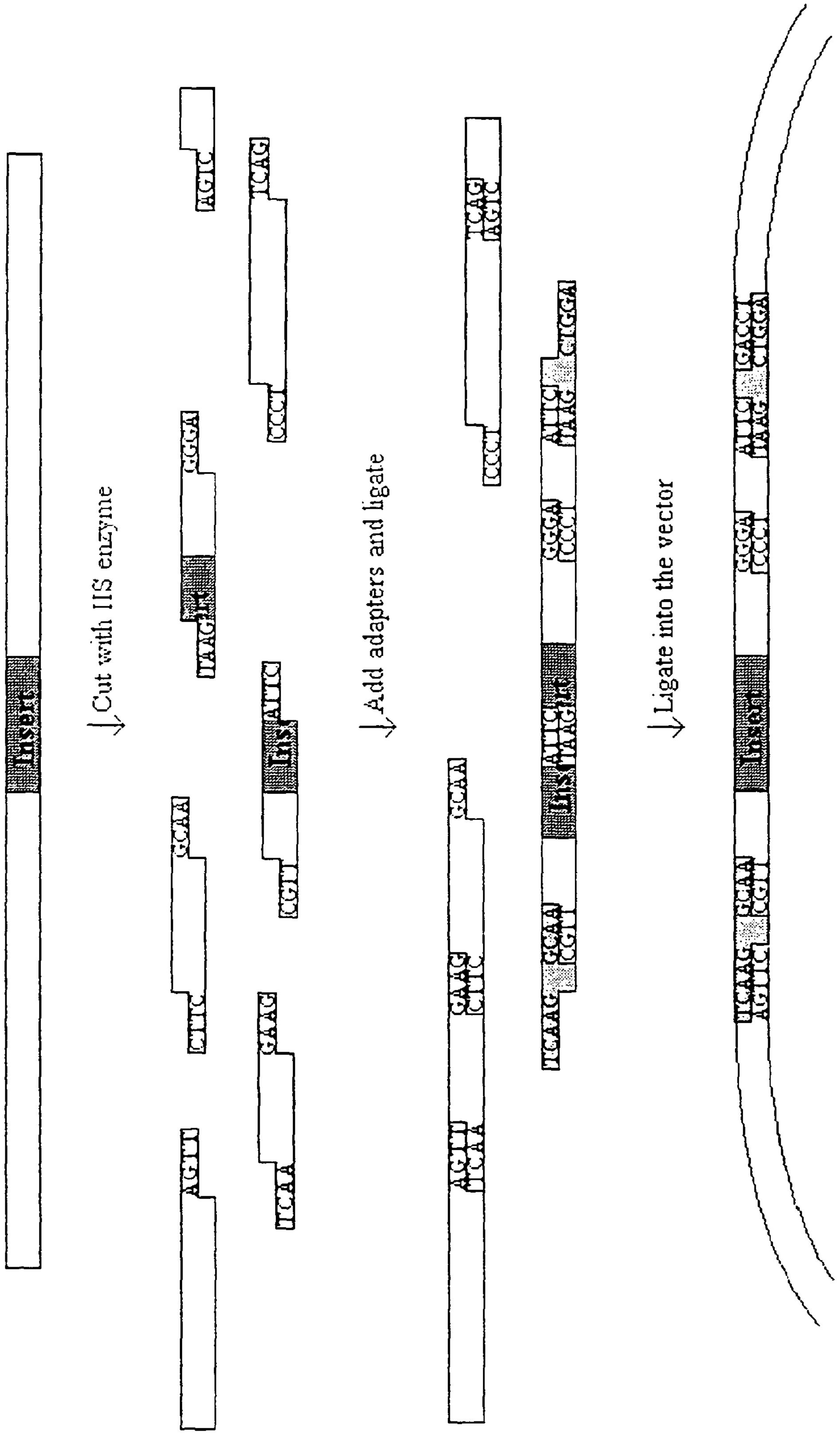

| | «0» starting fragments: | «1» starting fragments: |
|---|---|---|
| Position 1 | GGGG GGGG**AAA**<br>CCCCCCCCC | AAAAAAA**AAA**<br>TTTTTTTT |
| Position 2 | GGGG GGGG**AAC**<br>**TTT**CCCCCCCCC | AAAAAAA**AAC**<br>**TTT**TTTTTTTT |
| : | : | |
| Position 7 | GGGG GGGG**CCG**<br>**GCG**CCCCCCCCC | AAAAAAA**CCG**<br>**GCG**TTTTTTTT |
| Position 8 | GGGG GGGG<br>**GG**CCCCCCCCCC | AAAAAAA<br>**GG**CTTTTTTTT |

FIG. 2

| | Fragment 0 | Fragment 1 |
|---|---|---|
| Position 1.1 | GGGG GGGGAAA<br>CCCCCCCCC | AAAAAAAAAA<br>TTTTTTTT |
| Position 1.2 | **AAA**GGGG GGGGAAA<br>CCCCCCCCC | **AAA**AAAAAAAAAA<br>TTTTTTTT |
| Position 1.3 | **AAC**GGGG GGGGAAA<br>CCCCCCCCC | **AAC**AAAAAAAAAA<br>TTTTTTTT |
| : | : | |
| Position 8.1 | GGGG GGGG<br>GCCCCCCCCCC**TTT** | AAAAAAA<br>GCTTTTTTTT**TTT** |
| Position 8.2 | GGGG GGGG<br>GCCCCCCCCCC**TTG** | AAAAAAA<br>GCTTTTTTTT**TTG** |
| Position 8.3 | GGGG GGGG<br>GCCCCCCCCCC**TTC** | AAAAAAA<br>GCTTTTTTTT**TTC** |
| : | : | |

FIG. 3

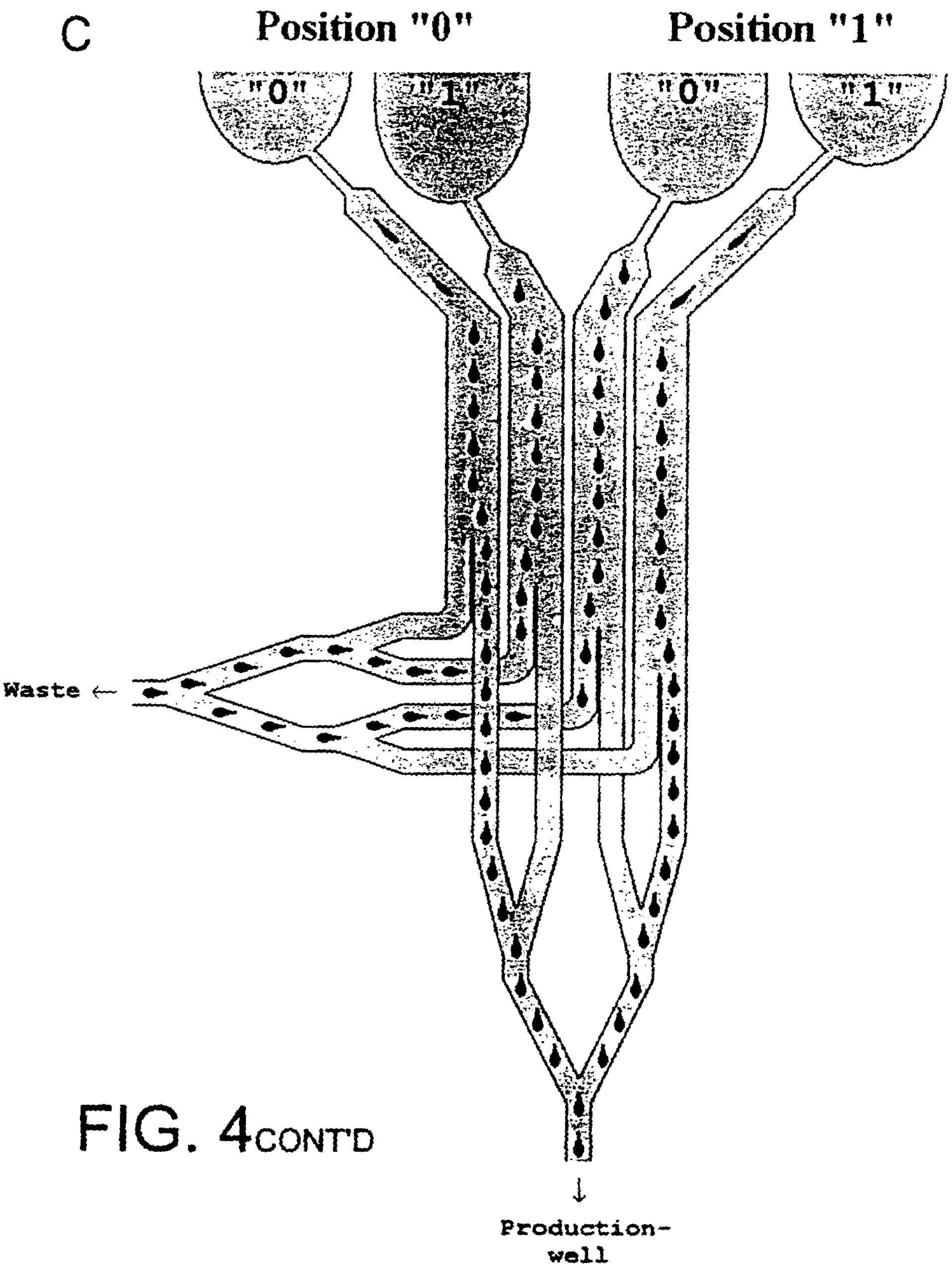
FIG. 4CONT'D

METHODS OF CLONING AND PRODUCING FRAGMENT CHAINS WITH READABLE INFORMATION CONTENT

The present invention relates to new methods of attaching first and second nucleic acid molecules, particularly methods of cloning in which adapter molecules mediate the binding between the first and second molecules, the resultant nucleic acid molecules thus formed and methods of generating DNA with a readily readable information content and kits for performing such methods.

Presently known cloning methods generally involve the use of restriction enzymes which are used to generate fragments for insertion and cleave vectors to produced corresponding and hence complementary terminal sequences. Generally, the enzymes which are used cut palindromic sequences and thus produce identical overhangs. Different sequences that are cut with the same restriction endonucleases can then be ligated together to form new, recombinant nucleic acids.

However, such methods suffer from a number of limitations. One disadvantage in using endonucleases that form two identical overhangs is the formation of different products on ligation. If for example two fragments A and B are to be ligated, as a consequence of common overhangs the products A+A and B+B as well as the desired A+B will be produced. Other by-products resulting from other fragments produced when A and B were formed will also be generated, e.g. reassociation into the original positions. It is therefore normal to use a separation process using agarose gels. The separation procedure however often results in a considerable loss of DNA.

Such methods necessarily suffer from various limitations including the by-products mentioned above, and the need to identify the desired end-products, e.g. if only a particular insert is to be cloned.

Other cloning techniques have been used in which cloning has been performed using PCR techniques, e.g. in which the PCR primers have IIS enzyme recognition sites. However, the use of PCR is disadvantageous in cloning techniques as it is time consuming and requires purification steps which result in significant loss of yield. The PCR reaction may also introduce point mutations and the like and the length of the fragment is limited to the polymerase capacity, e.g. a maximum of approximately 50 kb.

It has now surprisingly been found that by generating fragments with unique single stranded regions and then mediating the binding between a first and second nucleic acid molecule, many of these disadvantages may be avoided. In this method, restriction nucleases are used that form non-identical overhangs, e.g. type IP or IIS restriction endonucleases. As will be appreciated, if one uses a restriction endonuclease that makes overhangs of 4 base pairs, each fragment that is formed will have two overhangs of 4 base pairs each. It is theoretically possible therefore that $4^8$ (ie. 65,536) fragments may be formed with different combinations of the two overhangs. Thus, as a rule, each fragment formed on cleavage will have a unique pair of overhangs even when cleaving large nucleic acid molecules.

These unique overhangs may then be addressed and adjusted appropriately using adapters with two overhangs. For example in a cloning technique one of the overhangs is made to correspond to the overhang on the insert and the other overhang is made to correspond to the overhang on the vector into which the insert is to be introduced. This method is outlined in FIG. 1. In that case the DNA molecule containing the insert is cut with a restriction endonuclease which makes an overhang on each side of the insert. Each of the many fragments which are formed have different overhangs such that the two overhangs at either end of the insert are unique. Ligase is then added to bind two adapt corresponding single stranded regions. This leads to the formation of two new overhangs at the termini of the insert, which are selected such that they can be used to bind to the vector into which the insert is to be cloned. Providing identical overhangs are not created on other molecules only the desired insert will be ligated to the adapters. In the final step the insert is ligated into the vector which has two overhangs which complement the adapters' overhangs. The overhangs in the vector may be constructed using the same principles as described for the insert.

Thus in this new method, an adapter molecule is used which is complementary to a single stranded region generated on the first nucleic acid molecule and therefore binds to that molecule, but has a different single stranded region at its other terminus, thus effectively modifying the single stranded region presented for binding by the first nucleic acid molecule fragment. The adapter's free single stranded region may then mediate the binding of the first nucleic acid molecule fragment to a second nucleic acid molecule exhibiting a complementary single stranded region.

This method of mediation has particular applications for effectively identifying and selecting a first nucleic acid molecule fragment and then mediating its binding to a second nucleic acid molecule where this was not previously possible.

Of particular relevance to methods of cloning is the generation of fragments for cloning which have different single stranded regions at their termini relative to other fragments, which may then be selected and cloned into an appropriate vector. As described herein, such fragments are generated by the use of enzymes which cleave outside their recognition site and thus produce overhangs that depend on the sequence surrounding the recognition site which is likely to vary from fragment to fragment.

Such techniques may be used to direct only a single fragment to a particular vector or may be used to direct different fragments to different sites or indeed different vectors, even within the same reaction mix, providing appropriate adapters are constructed.

These methods have particular advantages over prior art methods. In particular, the whole procedure may be carried out in one or two steps, e.g. cutting and ligating simultaneously or cutting and ligating separately. Even in instances where the procedure is performed in two steps, it will often be possible to perform both steps in the same buffer, e.g. since T4 DNA ligase is known to work well in most buffers for restriction endonucleases. Time- and resource-consuming precipitation procedures may therefore be avoided. Moreover, ligations can be performed with overhangs of 4-6 bases, unlike conventional cloning where overhangs of 0-4 bases are used, thereby increasing ligation efficiency considerably.

Furthermore, the need to carry out gel separations may be avoided. The quantity of DNA required initially can be reduced substantially. Mutation of DNA molecules on UV exposure, a common occurrence in gel separation, may also be avoided. Furthermore, laboratory staff are not exposed to carcinogenic EtBr. Also, separation problems which can occur when restriction cleavage results in fragments of similar size may be avoided. The frequency of undesirable side-products such as empty vectors, too many inserts or incorrect orientation of the inserts may also be avoided.

Since it is generally not problematic if the insert is cleaved, a small selection, e.g of type IIS or Ip restriction endonucleases could provide far more cloning possibilities than a corresponding selection of ordinary type II restriction endonuclease used for conventional cloning procedures. Having a few type IIS, IP and similar restriction endonucleases that cleave with high frequency allows for many cloning possibilities.

In the specific instance of cloning of large DNA molecules (e.g. genomic DNA) or a solution containing many different DNA molecules in parallel (e.g. a cDNA library) it is very difficult to use conventional methods. If for example a large DNA molecule is cleaved with EcoRI, a large number of fragments may be formed with the same overhang, and in addition a considerable proportion of these fragments may be of roughly the same size. This may lead to the formation of a large number of undesired ligation products, even with gel separation. Moreover, gel separation can be difficult if the insert is large. Furthermore, it is also often difficult, or even impossible, to find restriction endonucleases that will not cut large inserts. These problems may be reduced/eliminated using the cloning procedure described herein.

If necessary, it is possible to increase the number of base pairs in the overhangs to (e.g.) 6 by using CjeI or similar endonucleases to form an even greater number of possible variables and thus increase the probability of producing unique overhangs.

The advantages of the method of the invention are even greater in complex cloning procedures. If several adapters are used for example, it is possible to clone many different inserts into one and the same vector at a corresponding number of different sites in one and the same reaction, as described hereinafter in more detail.

Deletions of small or large fragments may also be achieved using the same basic principle. This opens up the possibility of making complex recombinations of inter alia genomic DNA (removal of endogen viruses in genomes to be used for xenotransplantation, the insertion of a large number of genes from other genomes, new combinations of genes etc.). The method can also be used for exon-shuffling and other recombinations that are relevant in connection with artificial evolutionary systems.

Thus, in a first aspect, the present invention provides a method of attaching a fragment of a first nucleic acid molecule to a second nucleic acid molecule, wherein said method comprises at least the steps:

1) cleaving said first nucleic acid molecule with a nuclease which has a cleavage site separate from its recognition site to create at least one fragment of said first nucleic acid molecule having a single stranded nucleotide region (SS1a) at least one terminus of said fragment, 2) if necessary generating a single stranded nucleotide region (SS2) at least one terminus of said second nucleic acid molecule, 3) binding to at least one single stranded region of step 1) (SS1a) an adapter molecule comprising at one terminus a single stranded region (SSA1) complementary to the single stranded region of said first nucleic acid molecule fragment (SS1a) and additionally comprising at the other terminus a further single stranded region (SSA2) complementary to the single stranded region (SS2) at one terminus of said second nucleic acid molecule, 4) ligating said adapter to said first nucleic acid fragment, 5) binding said adapter to said second nucleic acid molecule, and 6) ligating said adapter to said second nucleic acid molecule.

As used herein, said first and second nucleic acid molecules are any naturally occurring or synthetic polynucleotide molecules, e.g. DNA, such as genomic or cDNA, PNA and their analogs, which are double stranded and in which single stranded regions may be generated.

Fragments of the first nucleic acid molecule are generated by use of a nuclease which cleaves outside its recognition site. One or more fragments may be generated depending on the sites which are cleaved (e.g. if the site is at the extreme end of the molecule only a few bases may be removed rather than the production of 2 fragments). Other nucleic acid molecule fragments described herein may be generated by any appropriate means, as mentioned herein, including the techniques used to produce the first nucleic acid molecule fragments. Fragments are preferably more than 10 bases, e.g. 10 to 200 bp, preferably more than 100 bases in length. For cloning applications, fragments having lengths in excess of 200 bases, e.g. from 200 bases to 2 kb may be used. Where longer single stranded regions are generated, fragments of longer lengths are also contemplated, e.g. 10-100 kb or longer.

"Single stranded regions" as referred to herein are regions of overhang at the end, ie. at the terminus of the first, second or third nucleic acid molecules or adapter molecules. These regions are sufficient to allow specific binding of molecules having complementary single stranded regions and subsequent ligation between these molecules. Thus, the single stranded regions are at least 1 base in length, preferably 3 bases in length, but preferably at least 4 bases, e.g. from 4 to 10 bases, e.g. 4, 5 or 6 bases in length. Single stranded regions up to 20 bases in length are contemplated which will allow the use of fragments in the method of the invention which are up to Mb in length.

"Binding" as used herein refers to the step of association of complementary single stranded regions (ie. non-covalent binding). Subsequent "ligation" of the sequences achieves covalent binding.

"Complementary" as used herein refers to specific base recognition via for example base-base complementarity. However, complementarity as referred to herein includes pairing of nucleotides in Watson-Crick base-pairing in addition to pairing of nucleoside analogs, e.g. deoxyinosine which are capable of specific hybridization to the base in the nucleic acid molecules and other analogs which result in such specific hybridization, e.g. PNA, DNA and their analogs. Complementarity of one single stranded region to another is considered to be sufficient when, under the conditions used, specific binding is achieved. Thus in the case of long single stranded regions some lack of base-base specificity, e.g. mis-match, may be tolerated, e.g. if one base in a series of 10 bases is not complementary. Such slight mismatches which do not affect the ultimate binding and ligation of the single stranded regions are considered to be complementary for the purposes of this invention. The single stranded regions may retain portions, on binding, which remain single stranded, e.g. when overhangs of different sizes are employed or the complementary portions do not comprise all of the single stranded regions. In such cases, as mentioned above, providing binding can be achieved the single stranded regions are considered to be complementary. In those cases, prior to ligation, missing bases may be filled in e.g. using Klenow fragment, or other appropriate techniques as necessary.

"Adapters" as referred to herein are molecules which adapt the first nucleic acid molecule fragment for binding to a second or third nucleic acid molecule. Adapter molecules comprise at least two regions. A first portion containing a single stranded region which is complementary to the single stranded region on the first nucleic acid molecule fragment and a second portion containing a single stranded region which is complementary to the single stranded region on the second nucleic acid molecule. The single stranded regions are as described hereinbefore and are preferably on different strands making up the adapter molecule. The above mentioned portions are at least as large as the single stranded regions, e.g. 4 to 6 bases in length, although they may be longer, e.g. up to 20 bases in length.

A linking region between these single stranded regions is required for the stability of the molecule. Conveniently this comprises a double stranded nucleic acid fragment, especially in methods of cloning where amplification, replication and/or translation are to be performed. However, this portion may be substituted by any appropriate molecule depending on the end use of the resulting ligated molecule. Clearly, to achieve ligation between the first and second nucleic acid molecules appropriate attachment points and moieties for ligation must be provided.

The linking portion may serve more than just a linking function and may for example provide sequences appropriate for primer or probe binding, e.g. for amplification or identification, respectively, or may contain integration sites for mobile elements such as transposons and the like. Depending on how the method is performed, the adapters preferably do not contain restriction sites for any restriction enzymes used in the method of the invention thus avoiding the need to inactivate or remove the enzymes prior to the addition of the adapters.

Conveniently adapter molecules may be exclusively comprised of a nucleic acid molecule in which the various properties of the adapter are provided by the different regions of the adapter.

Conveniently adapters are made up of two complementary oligonucleotides having between 10 and 100 bases each, e.g. between 20 and 50 bases.

In the method described above, preferably at least one first nucleic molecule fragment is generated having a single stranded region at either end (SS1a and SS1b) to each of which an adapter binds.

Preferably the method described herein is used for cloning. Thus, in the method described above, an adapter is bound at either end of the first nucleic acid molecule fragment (in which the adapters may be the same of different), and the unbound end of the first adapter is bound to the second nucleic acid molecule and the unbound end of the second adapter binds either to the second nucleic acid molecule (ie. at the other end distal to the binding of the first adapter, thereby forming a circular molecule) or binds to a third nucleic acid molecule. The first of these two alternatives may arise through cleavage of a circular vector to give rise to the second nucleic acid molecule to which the [adapter 1]:[first nucleic acid molecule fragment]:[adapter 2] insert is bound to re-circularize the vector. Alternatively, a linear or circular vector may be cleaved giving rise to two or more discrete fragments (herein the second and third nucleic acid molecules) which may be joined by the adapter 1:first nucleic acid molecule:adapter 2.

Thus, in a preferred feature, a first nucleic acid molecule fragment is generated which has a single stranded nucleotide region at either terminus (SS1a and SS1b), each of which is bound by an adapter, which may be the same or different, and the first of said adapters is bound to said second nucleic acid molecule and the second of said adapters binds either to said second nucleic acid molecule or to a third nucleic acid molecule.

Thus, alternatively stated, in a preferred embodiment, the present invention provides a method of cloning a fragment of a first nucleic acid molecule into a second nucleic acid molecule, wherein said method comprises at least the steps:

1) cleaving said first nucleic acid molecule with a nuclease which has a cleavage site separate from its recognition site to create one or more fragments of said first nucleic acid molecule, wherein at least one fragment has a single stranded nucleotide region at both termini (SS1a and SS1b), 2) cleaving said second nucleic acid molecule to create at least two single stranded regions (SS2a and SS2b) at the site of said cleavage (e.g. linearizing a circular vector or producing fragments in a linear or circular vector), 3) binding to one of the single stranded regions of step 1) (SS1a)

- a first adapter molecule comprising at one terminus a single stranded region (SSA1) complementary to the single stranded region of said first nucleic acid molecule fragment (SS1a) and additionally comprising at the other terminus a further single stranded region (SSA2) complementary to one of the single stranded regions (SS2a) produced by cleavage of said second nucleic acid molecule, and binding to a second single stranded region of step 1) (SS1b)
- a second adapter molecule as defined above which binds to the second single stranded region of said first nucleic acid molecule fragment (SS1b) and to the second single stranded region (SS2b) produced by cleavage of said second nucleic acid molecule, 4) ligating said adapters to said first nucleic acid fragment, 5) binding said, adapters to said second nucleic acid molecule or fragments thereof, and 6) ligating said adapters to said second nucleic acid molecule or fragments thereof.

In instances in which cleavage of the second nucleic acid molecule results in the production of two or more discrete fragments which become ligated to the first nucleic acid molecule fragment via the adapters, said fragments constitute second and third nucleic acid molecules of the invention.

Preferably, to prevent concatermirisation of [adapter:first nucleic acid fragment:adapter] units, the single stranded region of the second and third nucleic acid molecules which bind to these adapters are not complementary. Thus, for example, where cloning into a vector is performed, preferably said vector is linearized and at least of portion of said vector is removed from one terminus of that vector, e.g. at least two cleavage events occur.

In such methods, particularly for cloning, the second nucleic acid molecule, e.g. into which a first nucleic acid molecule fragment is inserted is conveniently a vector (or a part thereof, e.g. where the second and third nucleic acid molecules together comprise the vector, and result through its cleavage). Such vectors include any double stranded nucleic acid molecule which may be linear or circular. (However, as mentioned above in respect of the adapters, providing single stranded regions exist, or are generated at the termini of the second nucleic acid or its fragments (e.g.

the vector), the adjacent regions may be made up of any molecule providing ligation at the termini to the adapters is not compromised.)

Conveniently such vectors may contain sequences which aid their use in methods of the invention or their subsequent manipulation. Thus, vectors are conveniently selected with only two or a small number of restriction cleavage sites for the method of cleavage used. Thus for example where restriction enzymes are used, the vector is selected to include only a minimal number, preferably only two recognition sites to that enzyme.

Vectors may additionally comprise further portions or sequences for cloning, selection, amplification, transcription or translation as appropriate. Thus vectors may be used with probe or primer sites, promoter regions, other regulatory regions, e.g. expression control sequences etc. Conveniently well-known cloning vectors are employed, such as pBR322 and derived vectors, pUC vectors such as pUC19, lambda vectors, BAC, YAC and MAC vectors and other appropriate plasmids or viral vectors.

The molecule of which a fragment is to be inserted, ie. the first nucleic acid molecule, may be any molecule which can generate single stranded regions at least one of its ends using the nucleases described herein, although the central portion may be varied as appropriate. Preferably however such molecules are double stranded nucleic acid molecules and contain appropriate sites for the use of enzymes to create the single stranded overhangs which are required in accordance with the invention. Appropriately, the first nucleic acid molecule is derived from genomic DNA and the method of the invention is used to insert fragments thereof into appropriate vectors.

Adapters which may be used include short double stranded nucleic acid molecules with single stranded regions at their termini to longer molecules which may contain further sequences for example to allow selection as described hereinafter. Appropriate single stranded regions are selected on the basis of the terminal sequence of the first, second and third nucleic acid molecules or fragments thereof. Appropriate selection may also be used to direct the orientation of the insert, e.g. to produce clones which may be used to produce antisense nucleic acid molecules.

Adapters may be used in the methods of the invention in which their single stranded overhangs have already been generated, e.g. by the combination of single stranded complementary oligonucleotides which on hybridization leave overhangs at either ends, or by appropriate cleavage or digestion.

Alternatively, during the method of the invention, adapters may be modified to provide single stranded portions, e.g. by the use of restriction enzymes or other appropriate techniques during the course of the reaction. Conveniently, to simplify the number of steps, the enzymes used to generate single stranded regions in the first, second or third nucleic acid molecules (where necessary) may be used to generate the adapter single stranded regions.

As mentioned previously, the single stranded region may be 4 or more bases in length. When using longer overhangs or where the sequence of the full corresponding single stranded region of the first, second or third nucleic acid molecules is not known or unclear, a family of adapters with one or more degenerate bases in the single stranded region may be used, for example using methods to create libraries of adapters. Degenerate bases may also be used at positions prone to mis-match ligations.

For convenience a universal library of adapters may be created for use in the method of the invention. Thus for example, 16 different adapters with a 4 base-pair overhang consisting of two random bases (NN) and two bases specific to each adapter (e.g. AA, CC, . . . TT) may be created. In this way sufficient adapters may be created which are capable of distinguishing between 16 different first molecule fragment overhangs, which would suffice for many cloning purposes. Similarly a library of second molecule, e.g. vector overhangs may be created.

To increase the number of permutations in an adapter library, two separate oligonucleotide libraries may be generated, one with single stranded oligonucleotides with regions that will correspond to the single stranded region of the first nucleic acid molecule fragment and the second library with single stranded oligonucleotides with regions that will correspond to the single stranded region of the second nucleic acid molecule (e.g. vector). However in common in each member of the library is a complementary region, such that when one member from the first library is selected and combined with a member of the second library, they will hybridize leaving free the relevant single stranded regions. Thus for example to generate an adapter with an AA overhang and a TC overhang to bind to the first and second nucleic acid molecules respectively, members of the different libraries such as GGCCCCCNNAA[SEQ ID NO:1] may be combined with 3'-TCNNNCCGGGG-5'[SEQ ID NO:2] to form:

GGCCCCCNNAA[SEQ ID NO:1]
TCNNNCCGGGG[SEQ ID NO:2]

which exhibits the appropriate overhangs. When using only two 16 member libraries this allows the production of 256 different adapters.

In generating appropriate adapters conveniently the amount of mis-match which needs to be tolerated when binding to overhangs on first, second and/or third nucleic acid molecules should be reduced. This may conveniently be achieved by selecting oligonucleotides on the basis of the probability of a mismatch ligation being generated. A computer program for achieving this is described in more detail in Example 6. This method allows sets of oligonucleotides to be identified which can be used to construct chains with more than 100 fragments in a single ligation cycle but with very low levels of mis-match. Thus in a further feature the present invention provides computer software adapted to identify adapter molecules for use in the method of the invention.

As mentioned above, the production of fragments of said first nucleic acid molecule is achieved using a nuclease which has a cleavage site separate from its recognition site. In so doing, unique overhangs are created which reflect the sequence of that molecule. In a preferred feature, said nuclease is a class IP or IIS restriction enzyme or functional derivatives thereof. Such enzymes include enzymes produced synthetically through the fusion of appropriate domains to arrive at enzymes which cleave at a site distal to their recognition site.

These enzymes exhibit no specificity to the sequence that is cut and they can therefore generate overhangs with all types of base compositions. Cleavage with IIS enzymes result in overhangs of various lengths, e.g. from −5 to +6 bases in length. Preferably for performing the method of the invention, enzymes are chosen which generate 3-6, e.g. 4 base pair overhangs. Preferred enzymes for use in the invention include enzymes which produce 4 base overhangs at the 3' end: BstXI; 5 base overhangs at the 3' end: AloI, BaeI, BplI, Bsp24I; 6 base overhangs at the 3' end: CjeI, CjePI, HaeIV; 4 base overhangs at the 5' end: AceIII, Acc36I, Alw26I, AlwXI, Bbr7I, BbsI, BbvI, BbvII, Bvb16II, Bli736I, BpiI, BpuAI, BsaI, Bsc91I, BseKI, BseXI, BsmAI, BsmBI, BsmFI, Bso31I, Bsp423I, BspBS31I, BspIS4I, BspLU11III, BspMI, BspST5I, BspTS514I, Bst12I, Bst71I, BstBS32I, BstGZ53I, BstTS5I, BstOZ616I, BstPZ418I, Eco31I, EcoA41, EcoO44I, Esp3I, FokI, PhaI, SfaNI, Sth132I, StsI; and 5 base overhangs at the 5' end: HgaI Over 100 classes of IIS restriction endonucleases have been identified and there are large variations both with respect to substrate specificity and cleaving pattern. In addition, these enzymes have proved to be well suited to "module swapping" experiments so that one can create new enzymes for particular requirements (Huang-B, et al.; J-Protein-Chem. 1996, 15(5):481-9, Bickle, T. A.; 1993 in Nucleases (2nd edn), Kim-Y G et al.; PNAS 1994, 91:883-887). In these experiments the binding domain of transcription factor Sp1 was merged with the cleavage domain of FokI to construct a class IIS restriction endonuclease that makes a 4-base overhang with Sp1 sites. In other experiments a class IIS restriction endonuclease that cuts outside the binding sites of transcription factor Ultrabithorax was generated. Corresponding experiments have been conducted on class I enzymes. By merging the N-terminal part of the hsdS sub-unit of StyR 1241 (which recognizes $GAAN_6RTCG$[SEQ ID NO:82]) with the C-terminal part of the hsdS sub-unit of StyR 1241 (which recognizes $TCAN_7RTTC$[SEQ ID NO:83]) a new enzyme that recognizes the sequence $GAAN_6RTTC$[SEQ ID NO:84] was constructed. Several other experiments have been carried out with similar success. Unlike in the case of ordinary class II enzymes, it is therefore reasonable to assume that a number of new IIS and IP restriction enzymes can be constructed and adapted to cloning requirements that may arise in the future. Very many combinations and variants of these enzymes can therefore be used according to the principles described herein.

Generation of the single stranded regions on said first nucleic acid fragment may be achieved directly by cleavage of said first nucleic acid molecule with nucleases described herein without the development of intermediate molecules. This forms a preferred feature of the invention. Alternatively, indirect and more elaborate techniques may be used. For example, the first nucleic acid molecule or a fragment thereof may be "trimmed" using the nucleases described herein, in which linker molecules which carry the nuclease recognition site are bound to the first nucleic acid molecule or fragment thereof, and cleavage outside the recognition site results in cleavage within the first nucleic acid molecule or fragment thereof. This method is particularly useful since it takes advantage of the fact that T4 DNA ligase (and also other ligases) works well in most buffers used for restriction cutting. Ligation and cleavage can therefore be performed simultaneously in the same solution. Furthermore, this methods allows the generation of a unique overhang when the overhang generated by the first cleavage step is not unique.

The trimming procedure may be initiated using an "initiation linker" that is addressed to an overhang on the first nucleic acid molecule or fragment thereof, e.g. after cleavage with one or more restriction endonucleases as described herein. As used herein, a "linker" refers to a molecule which is similar to an "adapter" as described herein, except that the linker need only contain one single stranded region to allow binding to the molecule to be trimmed. Furthermore, the initiation linker contains one or more cleavage sites for nucleases that cleave outside their own recognition sequence, as described herein, for example BplI. The first nucleic acid molecule or fragment thereof should preferentially not contain cleavage sites for the IIS enzymes(s) used for the trimming procedure. Such cleavage sites may alternatively be inactivated prior to the trimming procedure (e.g. by methylation).

Propagation linkers (if used) and a termination linker (wherein the latter may be an adapter as described herein), T4 DNA ligase and the IIS enzyme(s) used for the trimming may be added together with the initiation linker. Once the initiation linker has been ligated into position, cleavage may be effected resulting in the generation of an overhang within the first nucleic acid molecule or fragment thereof. If desired (ie. if further trimming is required), a propagation linker containing degenerate overhangs may be used to ligate with the overhang which has been generated. Since the linker will also carry an appropriate nuclease recognition site, cleavage will again produce a further cleavage site further upstream into the first nucleic acid molecule or fragment thereof. This process will continue until an overhang is generated that is complementary to one of the overhangs in the termination linker (or adapter as described herein). This final linker will not itself have the nuclease recognition site and will therefore terminate trimming. As mentioned previously, this terminator linker may have an appropriate single stranded region for binding to the adapter used in the next step, or may itself be the adapter. An appropriate technique for performing the trimming method may be found in Examples 4 and 9.

The trimming method is preferably not performed with IIS enzymes belonging to the BcgI class (e.g. BplI, BaeI etc.) as the proteins are combined methylases and endonucleases and the methylase function may inactivate the binding sites on propagation linkers. Enzymes including FokI, HgaI etc. are therefore preferred enzymes for performing this method. If BcgI class enzymes are to be used, the cofactor AdoMet should be replaced with AdoHcy, Sinefungine or other cofactors that can not function as methyl donors.

Thus in a preferred feature the invention provides a method of removing the end terminus of a double stranded nucleic acid molecule with at least one single stranded region, comprising at least the steps of (i) binding (ie. ligated) a double stranded linker molecule containing a recognition site for a nuclease which cleaves outside its recognition site and a single stranded region complementary to the single stranded region on said double stranded nucleic acid molecule to said molecule and cleaving using said nuclease, thereby resulting in removal of one or more bases (e.g. 3-10, which may be in single or double stranded form, or a combination thereof) from the terminus of said nucleic acid molecule, (ii) optionally binding one or more propagation linkers which contain a recognition for a nuclease as described above and a degenerate single stranded region which binds to the overhang generated by the first or subsequent cleavage steps and cleaving using said nuclease, and (iii) adding a termination linker which binds to the single stranded region generated in steps i or ii.

A similar technique may be used to remove unwanted sequences, e.g. contributed by the adapter after ligation of the first nucleic acid molecule fragment and second (or third) nucleic acid molecules. Various techniques may be used to remove the unwanted sequences, e.g. if the sequence (e.g. a region from the adapter) contains a plant transposon sequence, this may be removed by adding necessary transposase enzymes to excise that sequence. Alternatively, the unwanted sequence may be removed by taking advantage of nuclease that cleave outside their recognition site. Thus, for example, adapters may be used which contain recognition sites for such enzymes which on cleavage (by appropriate selection of cleavage site sequences), result in overhangs generated at two distinct cleavage sites which are complementary and thus allow concomitant excision of the intervening sequence. Examples of techniques for removing intervening sequences are shown in Example 5. It will be appreciated that depending on the nuclease employed, it may be necessary to inactivate sites for that enzyme at locations other than adjacent to or within the intervening sequence.

Thus, in a further preferred feature, adapters as used herein, additionally comprise one or more nuclease recognition and cleavage sites whereby arrangement of said sequences allows, on cleavage, generation of complementary single stranded regions wherein each one of said pair of single stranded regions is generated by cleavage at a distinct site.

Depending on how the different steps in the method of the invention are performed, as described hereinafter, where necessary the second nucleic acid molecule, and/or the adapters may also be cleaved or digested to provide appropriate single stranded regions. In a preferred feature, the second nucleic acid molecule and/or the adapters are cleaved using the nucleases described above for generating the first nucleic acid molecule fragments. However, instead of cleavage with such nucleases, to generate appropriate single stranded regions and/or fragments from the second or third nucleic acid molecules or adapters, alternative techniques may be used. Thus for example other restriction enzymes, non-specific nucleases or appropriate exonucleases or mechanical methods such as sonication or vortexing may be used. Where enzymes are employed, small volumes are preferably used during the reactions to increase efficiency.

Ligation between the adapters and first, second and third nucleic acid molecules is achieved by any appropriate technique known in the art (see for example, Sambrook et al., in "Molecular Cloning: A Laboratory Manual", 2nd Ed., Editor Chris Nolan, Cold Spring Harbor Laboratory Press, 1989). For example, ligation may be achieved chemically or by use of appropriate naturally occurring ligases or variants thereof. Appropriate ligases which may be used include T4 DNA ligase, and thermostable ligases, such as Pfu, Taq, and TTH DNA ligase. Ligation may be prevented or allowed by controlling the phosphorylation state of the terminal bases e.g. by appropriate use of kinases or phosphatases. Appropriately large volumes may also be used to avoid intermolecular ligations. Thus, high adapter to vector/insert ratios may be used to avoid the vector or insert religating into its source material.

Other techniques may be used to avoid or remove vectors which become religated or which do not cleave. For example the insert may be cloned into a selection marker that destroys the host bacteria unless it has been inactivated by the insert. Alternatively restriction cleaving using restriction enzymes specific for the fragment removed from the vector may be performed after the ligation step. Religated and uncleaved vectors would be cleaved in this step. Thus, the ideal cloning site is therefore one which contains many unique restriction sites that are removed upon insert ligation. Alternatively well-known techniques may be used for identifying the desired product, e.g. gel separation.

If the steps of cleavage and ligation are performed together, advantageously the insert and the vector into which it is inserted do not contain binding sites for the nuclease used. Similarly, it is advantageous if the fragment removed from the vector during the process of cloning contains binding sites for the nuclease. In that case, if that fragment religates with the vector it would be cleaved and thereby removed again.

Once the first and second nucleic acid molecules (and optionally third nucleic acid molecules) or fragments thereof have been covalently attached, where necessary selection of appropriate products from any side-products may be performed. Selection may be performed by any techniques known in the art. Conveniently however, labelled probes may be used to identify sequences present only in the correct product, e.g. by probing for one or more sequences formed only through the union of the correct sequences, e.g. a probe directed to the junction between the adapter and the first, second or third nucleic acid sequences. Alternatively, the correct ligation may be detected by functional properties bestowed on the product through ligation, e.g. through the completion of sequences which allow expression of a particular product once the vector has been cloned into an appropriate host. Alternatively, selection may be performed by sequencing of the products which have been obtained, e.g. after amplification and/or transformation.

Appropriate labels include any moieties which directly or indirectly allow detection and/or determination through the generation of a signal. Although many appropriate examples exist, examples include for example radiolabels, chemical labels (e.g. EtBr, TOTO, YOYO and other dyes), chromophores or fluorophores (e.g. dyes such as fluorescein and rhodamine), or reagents of high electron density such as ferritin, haemocyanin or colloidal gold. Alternatively, the label may be an enzyme, for example peroxidase or alkaline phosphatase, wherein the presence of the enzyme is visualized by its interaction with a suitable entity, for example a substrate.

As mentioned previously, one of the significant advantages which this method offers over known methods is the simplification of the techniques which are required. The steps described herein may be performed sequentially in separate tubes (e.g. when different enzymes are used and cross-reaction is undesirable) or in a limited number of steps. However, ideally, the reaction is performed in a single step. This can be achieved by appropriate selection of enzymes, adapters and second/third nucleic acid molecules, e.g. vectors.

Thus for example the first nucleic acid molecule may be fragmented using a particular nuclease which is also used to fragment the second nucleic acid molecule. Since the enzyme used will cleave outside its recognition site, it would be expected that the resulting single stranded regions found on both the first and second nucleic acid molecule fragments will be unrelated. However, by appropriate choice of the mediating adapters (which may also be added providing they do not have restriction sites for that enzyme, or that cleavage at those sites reveals appropriate single stranded regions), these unrelated sequences may be linked via the intermediacy of the adapters. Thus the entire reaction may be performed in a single step.

It will also be appreciated that the adapters may be used to address the first nucleic acid fragments to different second nucleic acid fragments or cleavage sites. This would therefore allow different first nucleic acid molecule fragments to be directed and ligated to a particular vector or site within a vector. Thus multiple vectors (and corresponding appropriate adapters) may be used simultaneously and take up a single first nucleic acid molecule fragment.

Alternatively, multiple fragments or copies of the same fragment could be inserted at different sites within the same vector (in the latter case by the use of adapters with one common end but with the other end exhibiting variability to allow it to bind to different sites within the vector). In a further alternative, the first nucleic acid molecule fragments could be captured in the reverse orientation (again by appropriate adapter choice) and inserted into a vector, e.g. to produce antisense strands.

Thus in a preferred embodiment the method described herein is performed in a single step. The ligation steps (ie. adapter to first nucleic acid molecule fragment and final ligation) may however be conducted separately once association of the relevant molecules has been achieved. In a further preferred embodiment, the invention provides a method of simultaneously attaching two or more fragments of the first nucleic acid molecule to different second nucleic acid molecules (or different termini thereof). In cloning, this equates to the introducing of the two or more fragments into different sites in said second nucleic acid molecules or into different second nucleic acid molecules, e.g. into different sites within a vector or into different vectors.

Thus the present invention provides methods of the invention in which two or more fragments of the first nucleic acid molecule are attached to different second and optionally third nucleic acid molecules, or different termini thereof. In a preferred feature, methods are provided wherein one or more fragments of said first nucleic acid molecule are attached via adapters to single stranded regions in said second nucleic acid molecule resulting from different cleavage events. As a further preferred feature, methods are provided wherein one or more fragments of said first nucleic acid molecule are attached via adapters to single stranded regions in two or more second nucleic acid molecules.

It will be appreciated that even more complex reactions may be envisaged in which multiple first nucleic acid molecules (e.g. 2 or more, e.g. 2-10) are simultaneously cleaved in the same reaction and their fragments bound to appropriate adapters which direct them to bind to different second nucleic acid molecules, e.g. different vectors or sites in vectors.

Whilst the above described methods describe an especially simplified method, the above described effects may also be achieved by performing the method in discrete steps. This is particularly appropriate where different enzymes are used which would produce undesirable products in other molecules. Thus for example, different nuclease, such as restriction enzymes may be used to cleave the first and second nucleic acid molecules. In such cases, the molecules are cleaved separately, whereafter the enzymes are removed or inactivated before the fragments are mixed together with the adapters. Similarly, even if the same enzyme is used, if the adapters contain enzyme sensitive sites, the adapters could be appropriately modified to avoid reaction, e.g. by methylation, or the enzymes used to fragment the first and/or second nucleic acid molecules would be inactivated or removed (as mentioned above) prior to the addition of the adapters.

Conveniently, inactivation of enzymes may be achieved by incubation at least 65° C., e.g. for 20 minutes. Alternatively, appropriate techniques employing removal of the enzymes from the reaction, use of chelators, inhibitors etc. may be used to achieve inactivation.

Once appropriate clones have been generated and selected these may be treated according to standard methods of amplification, transformation, replication, expression, sequencing, depending on the proposed application of the clones. Other aspects of the invention thus include the nucleic acid molecule product of the method (ie. the nucleic acid molecule that is the [first nucleic acid molecule fragment]:[adapter]:[second nucleic acid molecule] product), such as cloning and expression vectors comprising that nucleic acid molecule product as well as transformed or transfected prokaryotic or eukaryotic host cells, or transgenic organisms containing a nucleic acid molecule produced according to the method of the invention.

Appropriate expression vectors include appropriate control sequences such as for example translational (e.g. start and stop condon, ribosomal binding sites) and transcriptional control elements (e.g. promoter-operator regions, termination stop sequences) linked in matching reading frame with the nucleic acid molecules of the invention. Appropriate expression systems are well known and documented in the art as well as methods for their introduction and expression in prokaryotic or eukaryotic cells or germ line or somatic cells to form transgenic animals. Appropriate expression vectors for transformation include bacteriophages and viruses, such as baculovirus, adenovirus and vaccinia viruses.

Kits for performing the methods described herein form a preferred aspect of the invention. Thus viewed from a further aspect the present invention provides a kit for attaching a first nucleic acid molecule fragment to a second nucleic acid molecule or a fragment thereof comprising at least (i) one or more adapters as described hereinbefore or means for producing such adapters, (ii) the second nucleic acid molecule and (iii) a nuclease which cleaves outside its recognition site, wherein the terminus of one of said adapters has a single stranded region complementary to a single stranded region generated on said second nucleic acid molecule after cleavage with said nuclease.

Preferably said kit comprises a library of oligonucleotides, e.g. as described herein, particularly as described in Example 3, from which appropriate adapters may be generated. The library of oligonucleotides as described herein forms a further preferred feature of the invention. Thus for example said library may comprise a plurality of oligonucleotides comprising 1) a plurality of oligonucleotides of the formula XNNNNN wherein X is one or more bases (wherein said bases are as described hereinbefore) and is invariant in all of said oligonucleotides and each N is a base at the 5' end which is varied in the different oligonucleotides, ie. to produce 1024 variants, 2) a plurality of oligonucleotides of the formula X'NNNN wherein X' is complementary to X and is invariant in all of said oligonucleotides and each N is a base at the 5' end as described hereinbefore, 3) a plurality of oligonucleotides of the formula YNNNNN wherein Y, which is not the same as X, is one or more bases (wherein said bases are as described hereinbefore) and is invariant in all of said oligonucleotides and each N is a base at the 3' end as described hereinbefore, and 4) a plurality of oligonucleotides of the formula Y'NNNNNN wherein Y' is complementary to Y and is invariant in all of said oligonucleotides and each N is a base at the 3' as described hereinbefore.

Optionally the kit may contain other appropriate components selected from the list including ligases, enzymes necessary for inactivation and activation of restriction or ligation sites, primers for amplification and/or appropriate enzymes, buffers and solutions, and a data carrier containing a computer program to assist in the selection of oligonucleotides from the above mentioned library. The use of such kits for performing the method of the invention form further aspects of the invention.

The above described method may be adapted to combine multiple first, second, third etc. nucleic acid molecules as described below. In this method multiple fragments are combined by appropriate selection of the single stranded regions which appear at their ends. This has application in the production of specific sequences for biological purposes, but has particular utility in the production of nucleic acid molecule chains in which the units making up the chains each denotes a unit of information, ie. the chains may be used to store information, as will be described in more detail below. As used herein "chain" refers to a serial arrangement of fragments as described herein. Such chains are preferably linear and include branched and unbranched fragment sequences. Thus, for example, branched DNA fragments may be used to provide chains with a branched arrangement of fragments.

To produce nucleic acid molecule chains with different unit fragments, ie. fragment chains the following method may be used. Firstly it is necessary to generate fragments which have overhangs at either end, to allow them to bind to one another. (The ultimate 3' and 5' fragments may however have an overhang at only the end which will become attached to internal fragments.) As will be described in more details below, for certain applications appropriate oligonucleotides may be derived from libraries in which the members exhibit variability in at least some of their bases. If libraries are to be produced in which the members are double stranded, it will be appreciated that the number of members in such a library could be rather high. This can however effectively be reduced by using a smaller number of smaller building blocks.

One strategy is to make two single-stranded oligonucleotides using conventional techniques. In the example described above (6 base double stranded linker and 3 base overhangs at either end), oligonucleotides having a region of 6 bases which complement each other and so allow hybridization may be used. Since not all of the molecules are involved in the hybridization, single stranded regions extend beyond the hybridizing region thus creating single stranded regions. Conveniently the number of required library members may be reduced even further if repeat sequences appear with frequency in the fragment chain. This will be described in more detail below.

Once the appropriate double stranded chain units (ie. fragments) have been created they may be ligated together in the same solution, providing the different overhangs present on the sequences are unique.

Thus in a further aspect, the present invention provides a method of synthesizing a double stranded nucleic acid molecule comprising at least the steps of:

1) generating n double stranded nucleic acid fragments, wherein at least n−2 fragments have single stranded regions at both termini and 2 fragments have single stranded regions at least one terminus, wherein (n−1) single stranded regions are complementary to (n−1) other single stranded regions, thereby producing (n−1) complementary pairs, 2) contacting said n double stranded nucleic acid fragments, simultaneously or consecutively, to effect binding of said complementary pairs of single stranded regions, and 3) optionally ligating said complementary pairs simultaneously or consecutively to produce a nucleic acid molecule consisting of n fragments.

The terms "nucleic acid molecule", "single stranded regions", "complementary", "binding" and "ligating" are as described hereinbefore.

In step 1) reference is made to (n−1) single stranded regions complementary to (n−1) "other" single stranded regions. This describes two families of single stranded regions, which together comprise 2(n−1) members, forming n−1 pairs. Thus "other" refers to single stranded regions in the second family which are not present in the first family.

"Contacting" as used herein refers to bring together the double stranded fragments under conditions which are conducive to association of the complementary single stranded regions. Depending on the method used, this may ultimately allow ligation of the fragments carrying those regions. It should however be noted that the fragments may be linked by methods other than ligation. For example PCR may be used with appropriate primers, e.g. pairs of primers.

Simultaneous or consecutive contacting and/or ligation refers to the possibility of adding the fragments individually or in groups to a growing chain or simultaneously adding all n fragments together, wherein ligation may be performed after each addition or once all n fragments have been combined. Preferably ligation is effected once all fragments have been combined.

"Fragments" as used herein are as defined herein before, but preferably are shorter in length. Thus fragments are preferably greater than 6 bases in length (wherein said length refers to the length of each single stranded oligonucleotide making up the fragment which may differ slightly in length from one another), e.g. between 6 and 50 bases, e.g. from 8 to 25 bases.

As referred to herein, "n" is an integer of at least 4, for example at least 10 or 100, e.g. between 25 and 200.

Preferably, as mentioned above, the fragments are generated by the use of single stranded oligonucleotides to generate appropriate double stranded molecules.

Of particular interest in such methods is the production of fragment chains that may be used to store information in the form of code which may readily be accessed.

There is currently a great need for storing information for different purposes (e.g. computer software, music, films, databases etc.). It has therefore been imperative to find efficient storage media, resulting in the development of CD ROMs, DVD technology etc. Nucleic acid molecules offer far more efficient methods for storing information and have several advantages over storage methods currently in use. For example, the storage capacity of nucleic acid molecules is vast. In principle, a test-tube containing DNA molecules may contain as much information as several million CD ROMs or more. Nucleic acid may be copied quickly and efficiently using natural systems which are greatly enhanced by techniques which have been developed such as PCR, LCR etc. When stored appropriately, nucleic acid molecules may be preserved for extremely lengthy periods. Naturally existing tools for manipulation of nucleic molecules are already available for processing of the molecules, e.g. polymerases, restriction enzymes, transcription factors, ribosomes etc. The nucleic acid molecules may also have catalytic properties.

Furthermore, nucleic acid molecules may be used as secure systems since they may be made such that they are not readily copied, unlike copying of current storage systems, e.g. CDs etc., which is increasingly prevalent.

Previously however, it was not possible to take advantage of the enormous potential offered by nucleic acid molecules due to the absence of any effective methods for writing DNA messages or reading DNA messages. The above described method provides methods which overcome this problem allowing the rapid synthesis of large DNA molecules and methods of rapidly and efficiently scanning those molecules to retrieve the information.

The key to effective retrieve of information encoded by the nucleic acid molecules produced according to the method described herein, is the expansion of the information providing unit in the molecule. In nature and in methods used previously, each base in the sequence has an individual informational content. Indeed methods have been described in which a single base may signify more than a single informational unit, e.g in binary code, the bases A="00", C="01", G="10" and T="11". Whilst this has advantages insofar as significant amounts of information can be contained in a single molecule, the system has serious drawbacks as it requires writing and reading methods in which individual bases may be attached and discriminated.

In a preferred method of the invention therefore, information units are provided which are not single bases, but are instead short sequences. The techniques described above allow the rapid production of such chains and the information may be readily accessed.

Thus units representing coded information may be generated and read. Each information unit may therefore represent an element of code, in which the code may for example be alphanumeric code or a simpler representation such as binary code. In each case it is necessary for individual elements of the code, e.g. "a", "b", "c", "1", "0" etc. to be represented by an individualized and specific sequence.

As used herein "information units" refer to discrete short sequences which represent a single piece of information, e.g. one or more (ie. combinations thereof) elements of a code.

"Elements" of code, as mentioned above, refer to the different members making up a code such as binary or alphanumeric code.

Thus, in a preferred embodiment of the method of the invention, the fragments which are linked together comprise regions representing a unit of information corresponding to one or more code elements. Preferably the code is alphanumeric. Especially preferably the code is binary. Thus for example, considering a binary system of information capture, if one wishes to produce chains consisting of "0", "1" fragments, appropriate sequence combinations may be attributed to "0" or "1".

Conveniently each of said one or more code elements (together) has the formula $$(X)_a,$$

wherein

X is a nucleotide A, T, G, C or a derivative thereof which allows complementary binding and may be the same or different at each position, and a is an integer greater than 2, e.g. greater than 4, for example from 2 to 20, preferably from 4 to 10, e.g. 6 to 8, wherein $(X)_a$ is different for each one or more code elements.

Especially preferably, in the case of binary code, the code elements "1" and "0" may have the formulae:

$$\text{"0"}=(X)_a \text{ and "1"}=(Y)_b,$$

wherein $(X)_a$ and $(Y)_b$ are not identical,

X and Y are each a nucleotide A, T, G, C or a derivative thereof which allows complementary binding and may be the same or different at each position, and a and b are integers greater than 2, e.g. greater than 4, for example from 2 to 20, preferably from 4 to 10, e.g. 6 to 8.

As referred to herein, a "derivative" which is capable of complementary binding refers to a nucleotide analog or variant which is capable of binding to a nucleotide present in a complementary strand, and includes in particular naturally occurring or synthetic variants of nucleotides, e.g uracil or methylated, amidated nucleotides etc.

In its simplest and preferred form, X and Y are the same at each position, e.g. "0"=GGGGGGGG and "1"=AAAAAAAA. However, repeat sequences such as $[AC]_6A$ or $[GT]_6A$ may be used. The code sequence may also have a functional property, e.g. it may be an integration element such as AttP1 or AttP2.

It will however be appreciated that the sequences described above may also denote more than a single code element. Thus for example the information unit may denote 2 or more code elements, e.g. from 2 to 32 element, preferably from 2 to 4 code elements. If for example binary code is considered, each information unit may refer to "01" or "00" or "11" or "10".

In the method described herein, chains comprising such features may be prepared as follows. To produce a chain with for example 8 0/1 fragments, eight "0" starting fragments with different overhangs and 8 "1" starting fragments with different overhangs are generated as illustrated in FIG. 2. In this case "0" fragments consist of the sequence GGGGGGGG, although this could be replaced by other sequences. In addition the fragments are synthesized such that they have unique overhangs such that they may only be ligated at one position. Thus, the fragments for position 1 in the chain are produced such that they have an overhang which is complemented by one of the overhangs in the fragments for position 2. Thus, the position 2 fragments are synthesized such that they can bind to position 1 fragments. Similarly position 3 fragments may only bind to position 2 fragments at one of their termini and position 4 fragments at the other terminus and so forth. These fragments are stored separately. In order to build up a chain, selection is made from one of the two alternative for each position such that an appropriate binary chain is produced.

Thus, in the scheme outlined above, to produce a fragment chain which represents a chain 01001011, "0" fragments from positions 1, 3, 4 and 6 are mixed with "1" fragments from positions 2, 5, 7 and B. If the fragments are then ligated together by adding ligase or using other ligation methods mentioned previously, the above described chain will be produced. As will be appreciated, this chain could also be achieved using for example only 4 fragments if the information unit carried on each fragment denoted 2 code elements.

It is furthermore possible to combine intermediate fragment chains (e.g. containing at least 4 fragments) with other fragment chains, which providing appropriate overhangs exist at their termini may be ligated together to form composite fragment chains. Thus, several cycles could be conducted in parallel and the products combined. In the method shown in FIG. 2, the end fragments have blunt ends, but clearly, appropriate fragments could be used that similarly have overhangs at the termini.

An appropriate technique for producing 8 fragment chains, each containing 8 fragments which can then be ligated together is illustrated in FIG. 3. For fragment chain 1, end fragments are used such that it is possible for the completed fragment chain to ligate to fragment chain 2 and so on. These may then be combined to produce a 64 fragment chain. Similarly, 8 such fragment chains may be combined to produce fragment chains comprising 512 fragments.

As will be appreciated, as with the production of shorter chains, the step of ligation, when performed, is conveniently effected once all the fragment chains have been combined.

However, the step of ligation may be performed sequentially if desired on addition of each subsequent fragment chain.

To combine 8 binary fragments per cycle, 16 different starting fragments are required, representing the different "0", "1" alternatives at each position. To make a chain of 64 fragments using two cycles, ie. to produce 8 chains with 8 fragments which are then ligated, only 16+(4×7)=44 starting fragments are required. Thus, the number of different starting fragments required reflects an almost linear increase in contrast to the combinations of the fragment chains which can be produced which increases exponentially with the number of cycles. As a consequence, very long fragment chains may be produced with a relatively small number of starting fragments.

Of course, as mentioned previously, intermediate chains longer or shorter than 8 may be produced. Since a large number of permutations exist in the overhang region, more starting fragments may be used thus allowing larger fragments to be built up in a single cycle. Thus, the number of cycles necessary to produce long chains may be reduced.

Small fragment chains produced according to the methods described herein may also be attached together by using variations of the techniques described herein. For example, complementary primer pairs may be used to link the various chains as described in Example 8. In this technique, amplification of the fragment chains is achieved using different primer pairs. The second primer in primer pair 1 is complementary to the first primer in primer pair 2 and the second primer in that pair is complementary to the first primer in primer pair 3 and so on. PCR reactions are then performed which produce products which in single stranded form are able to bind to one another through their complementary ends introduced by the primer pairs. These may then be ligated together.

Alternatively, fragment chains prepared by the methods described herein may be amplified with a primer which contains a restriction site to a nuclease which cleaves outside its recognition site. These amplification products are then digested with that nuclease to produce non-palindromic overhangs in the end of each fragment chain. By appropriate sequence selection (e.g. in the primer or fragments which are used) the overhangs which are generated allow the different fragment chains to be combined in order.

In a preferred aspect therefore, the invention provides a method of synthesizing a double stranded nucleic acid molecule comprising at least the steps of:

1) generating fragment chains according to the method described hereinbefore;

2) optionally generating single stranded regions at the end of said fragment chains, wherein said single stranded regions are complementary to other single stranded regions on said fragment chains thus forming complementary pairs of single stranded regions;

3) contacting said fragment chains with one another, simultaneously or consecutively, to effect binding of said complementary pairs of single stranded regions.

Optionally said chains are ligated together, however, alternative techniques may be use to form the ultimate chain, e.g. PCR may be used as described herein.

Preferably intermediate fragment chains are between 4 and 20 fragments in length, e.g. 5 to 10, and between 5 and 50 such fragment chains are combined e.g. between 10 and 20.

Conveniently fragments to be used in the method of the invention are contained within libraries. Methods of producing the fragments which make up the library are well known in the art. For example a series of oligonucleotides may be produced which comprise two portions. A first portion which will form an overhang at one end and a second portion which will effect binding to a complementary oligonucleotide and which contains within that portion the information unit. By producing common hybridizing portions and variant overhangs, a series of double stranded oligonucleotides for one or more code elements (denoted by at least a part of the hybridizing portion) are created. This provides a library for one (or a combination of) code elements. Different libraries may be created for different code elements (or combinations thereof), by appropriate alteration of the information unit, ie. the sequence in the hybridizing portion.

Conveniently for use in the invention, these different double stranded oligonucleotides are arranged in 2 dimensional arrays such that in one dimension consecutive positions within the ultimate fragment are indicated and in the second dimension the possible code element (or combinations thereof) are provided. In the simplest case, in binary code, in which "0" and "1" are represented by different sequences, the first dimension would comprise fragments for each position of the proposed fragment and the second dimension would have only 2 variants ("0" and "1"). This may be viewed as a single library or two libraries, ie. the "0" or "1" libraries. Once these libraries are produced, fragment chains with any desired order of fragments may be readily produced.

In order to appropriately direct library members to their correct site or well (ie. the library may be comprised of separate solid supports, or a solid support with different addresses, e.g. wells, or different wells containing different solutions), any appropriate sorting technique may be used. This sorting may be achieved by virtue of the process used for production of the library members, or sorting may be achieved by an appropriate technique, e.g. by binding to complementary oligonucleotides at the relevant library site.

Appropriate solid supports suitable for attaching library members are well known in the art and widely described in the literature and generally speaking, the solid support may be any of the well-known supports or matrices which are currently widely used or proposed for immobilization, separation etc. in chemical or biochemical procedures. Thus for example, the immobilizing moieties may take the form of beads, particles, sheets, gels, filters, membranes, microfibre strips, tubes or plates, fibres or capillaries, made for example of a polymeric material e.g. agarose, cellulose, alginate, teflon, latex or polystyrene. Particulate materials, e.g. beads, are generally preferred. Conveniently, the immobilizing moiety may comprise magnetic particles, such as superparamagnetic particles.

In a preferred embodiment, plates or sheets are used to allow fixation of molecules in linear arrangement. The plates may also comprise walls perpendicular to the plate on which molecules may be attached. Attachment to the solid support may be performed directly or indirectly and the technique which is used will depend on whether the molecule to be attached is an oligonucleotide for fixing the library member or the library member itself. For attaching the library members directly, ie. not via binding to an oligonucleotide, conveniently attachment may be performed indirectly by the use of an attachment moiety carried on the nucleic acid molecules and/or solid support. Thus for example, a pair of affinity binding partners may be used, such as avidin, streptavidin or biotin, DNA or DNA binding protein (e.g. either the lac I repressor protein or the lac operator sequence to which it binds), antibodies (which may be mono- or polyclonal), antibody fragments or the epitopes or haptens of antibodies. In these cases, one partner of the binding pair is attached to (or is inherently part of) the solid support and the other partner is attached to (or is inherently part of) the nucleic acid molecules. Alternatively, techniques of direct attachment may be used such as for example if a filter is used, attachment may be performed by UV-induced crosslinking. When attaching DNA fragments, the natural propensity of DNA to adhere to glass may also be used.

Oligonucleotides to be used for capture of the library members may be attached to the solid support via the use of appropriate functional groups on the solid support.

Attachment of appropriate functional groups to the solid support may be performed by methods well known in the art, which include for example, attachment through hydroxyl, carboxyl, aldehyde or amino groups which may be provided by treating the solid support to provide suitable surface coatings. Attachment of appropriate functional groups to the nucleic acid molecules of the invention may be performed by ligation or introduced during synthesis or amplification, for example using primers carrying an appropriate moiety, such as biotin or a particular sequence for capture.

In a further aspect therefore the present invention provides a library of fragments as defined herein comprising $(n)_m$ fragments, wherein n is as defined hereinbefore and corresponds to the length of chain that said library may produce, and m is an integer corresponding to the number of possible code elements or combinations thereof, such that fragments corresponding to all possible code elements for each position in the final chain are provided.

Portions of said libraries in one dimension, ie. comprising n fragments for only a single code element (or combinations thereof) or comprising m fragments representing all code elements (or combinations thereof) for a single position on the chain, form further aspects of the invention.

Appropriate mixing may be achieved by automation. For example in the case of "0", "1" fragments, the correct combination of these elements is the critical step in terms of resource- and time-consumption. This method is described in more detail in Example 2. In particular, the procedure may be miniaturised providing appropriate amplifying methods (such as cloning and/or PCR) are employed in the last step. Thus, techniques using technology such as sorting using flow cytometers may be employed as described in FIG. 4C. Such sorting procedures are well established and are able to sort approximately 5-30000 droplets per second for standard equipment, but up to 300000 droplets per second for the most advance cytometers.

As mentioned previously, it is possible that each fragment may denote more than a single code element. If for example, each fragment denotes 5 code elements, using existing technology and a library of 32×100 library components, if 3200 containers were connected to a sorting device illustrated in FIG. 4C, it should be possible to write several thousand chains with 500 code elements per second. Clearly, a method which can generate nucleic acid sequences with such rapidity offers significant advantages over known methods in the art.

The nucleic acid molecule (ie. the fragment chain) produced according to the above described method and the single stranded molecules thereof comprise further features of the invention. These molecules may as appropriate be included into a vector, as described hereinbefore.

Once produced, the fragment chains, in double stranded or single stranded form, may be used in various applications, as described hereinafter. One application of particular utility is to store information. In such cases appropriate means of reading the information stored in those chains is required. In some applications, fragment chains may be appropriately addressed to particular sites, e.g. through binding to oligonucleotides carried on solid supports which are complementary to overhangs on one terminus of the fragment chains. Alternatively appropriate antibody/antigen, or DNA:protein recognition systems may be used. Thus, information stored in molecules addressed in this way, or in solution may then be accessed.

Co-pending application PCT/GB99/04417, a copy of which is appended hereto, describes appropriate techniques for addressing and reading information contained in nucleic acid molecules. Of particular note in this respect are techniques in which fluorescence of probes carrying fluorescent labels directed to particular sequences are detected. In such techniques, probes, carrying labels as described hereinbefore, may be directed to particular fragment regions, particularly to regions denoting code elements. The signals generated (directly or indirectly) by those labels may then be detected and the code element thereby identified. If a simple binary system is used only 2 discrete labels are required and their pattern of binding may be determined. Alternatively, if a more complex code is reflected in the fragment chains, correspondingly more discrete labels are required for unambiguous detection.

Thus in a further aspect, the present invention provides, a method of identifying the code elements contained in a nucleic acid molecule prepared as described hereinbefore (ie. fragment chain) wherein a probe, carrying a signalling means (e.g. a label), specific to one or more code elements, is bound to said nucleic acid molecule and a signal generated by said signalling means is detected, whereby said one or more code elements may be identified.

Preferably said signalling means is a label as described hereinbefore.

A "probe" as referred to herein refers to an appropriate nucleic acid molecule, e.g. made up of DNA, RNA or PNA sequences, or hybrids thereof, which is able to bind to the target nucleic acid molecule (which may be single or double stranded) through specific interactions, ie. is specific to particular code elements, e.g. through complementary binding to a particular sequence. Probes may be any convenient length, to allow specific binding, e.g. in the order of 5 to 50 bases, preferably 8 to 20 bases in length.

A "signalling means" as used herein refers to a means for generating a signal directly or indirectly. A signal may be any physical or chemical property which may be detected, e.g. presence of a particular product, colour, fluorescence, radiation, magnetism, paramagnetism, electric charge, size, or volume. Preferably the label is a fluorophore whose florescence is detected. In such cases fluorescence scanners may be used for detection of the label and thereby identification of the code elements.

A particular code element or combination of elements may be identified by the appearance of a particular signal. Clearly the position of each signal is crucial to determining the sequence of the code elements. As a consequence methods in which positional information (absolute or relative) may be obtained should be used. Appropriate techniques, e.g. using target molecules which have been attached to a solid support at one end, are described in co-pending application PCT/GB99/04417.

A number of applications exist for the fragment chains once produced in nano and pico-technology, inter alia for example by stretching of the fragment chains by means of a stream of liquid, electricity or other technology and using them as templates for nano and pico-structures. The products may also be used to label products which can then be screened to establish their identity. Alternatively, the molecules may be used to store information, e.g. pictures, text, music or as data storage in DNA computers. The rapid production and reading techniques makes such applications possible for the first time.

Kits for performing the methods described above form a preferred aspect of the invention. Thus viewed from a further aspect the present invention provides a kit for synthesizing a double stranded nucleic acid molecule comprising at least n double stranded nucleic acid fragments, wherein at least n−2 fragments have single stranded regions at both termini and 2 fragments have single stranded regions at least one terminus, wherein (n−1) single stranded regions are complementary to (n−1) other single stranded regions, thereby producing (n−1) complementary pairs. Preferably in excess of n fragments are supplied for production of a chain of n fragments, such that selection of appropriate fragments for different positions is possible. Thus in a preferred feature said kit comprises $(n)_m$ fragments, wherein n is as defined hereinbefore, and m is an integer corresponding to the number of possible variations, e.g. unique sequences or code elements or combinations thereof, such that fragments corresponding to all possible sequences or code elements for each position in the final chain are provided. Preferably these fragments are provided in appropriate libraries arranged with reference to their position within the fragment chain and the code element(s) which they represent, such that desired fragments may be readily selected from the array.

Optionally the kit may contain other appropriate components selected from the list including ligases, enzymes necessary for inactivation and activation of restriction or ligation sites, primers for amplification and/or appropriate enzymes, buffers and solutions. The use of such kits for performing the method of the invention form further aspects of the invention.

Figure 4:
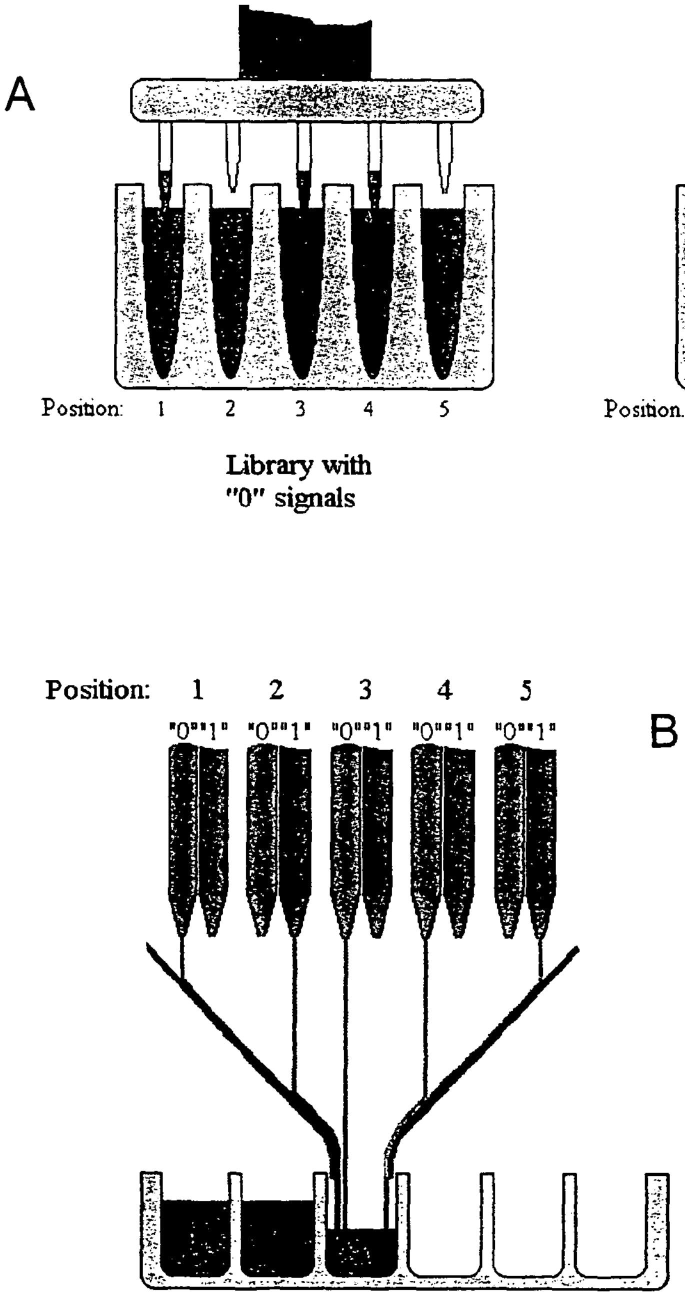
Figure 5:
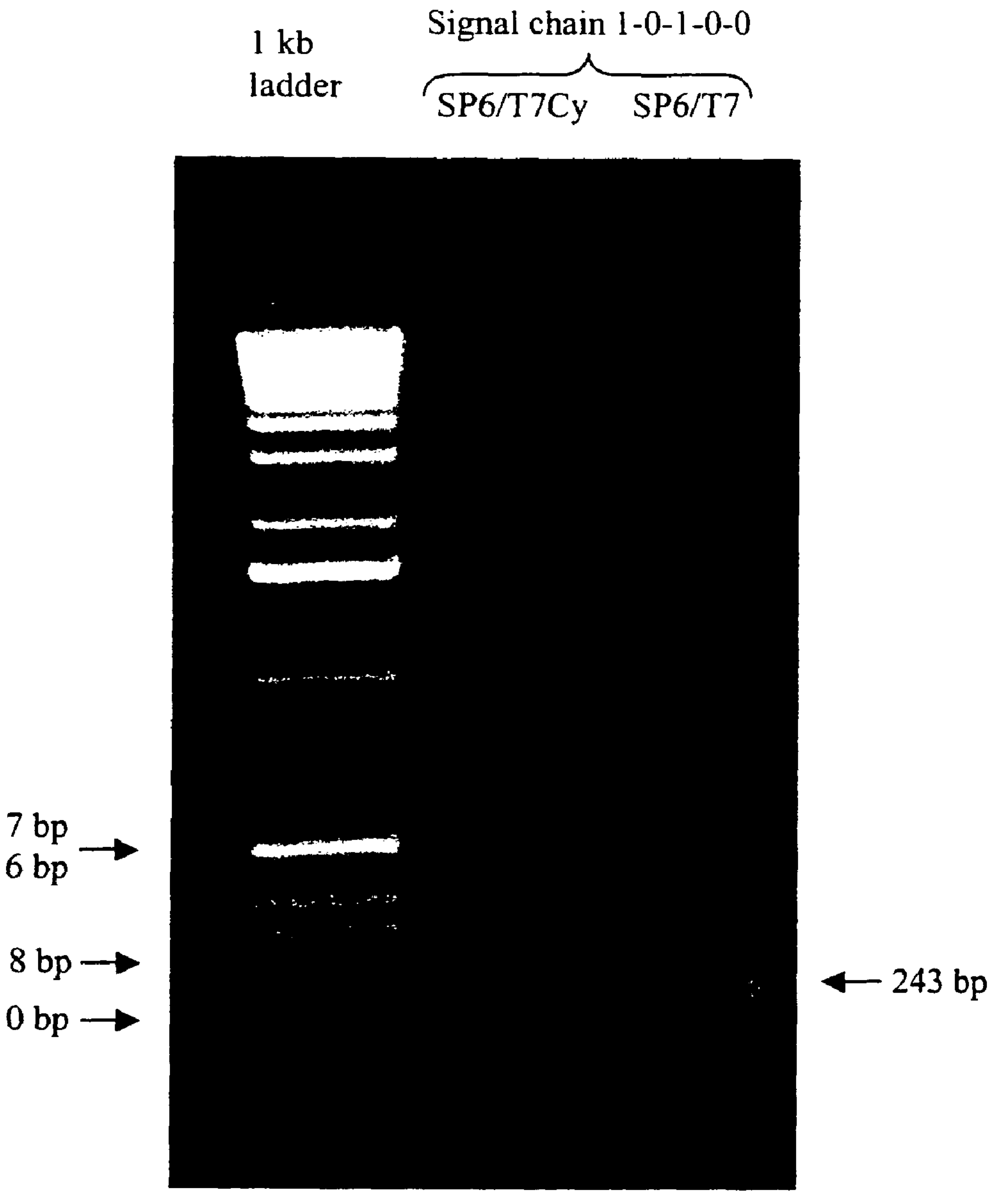
Figure 6:
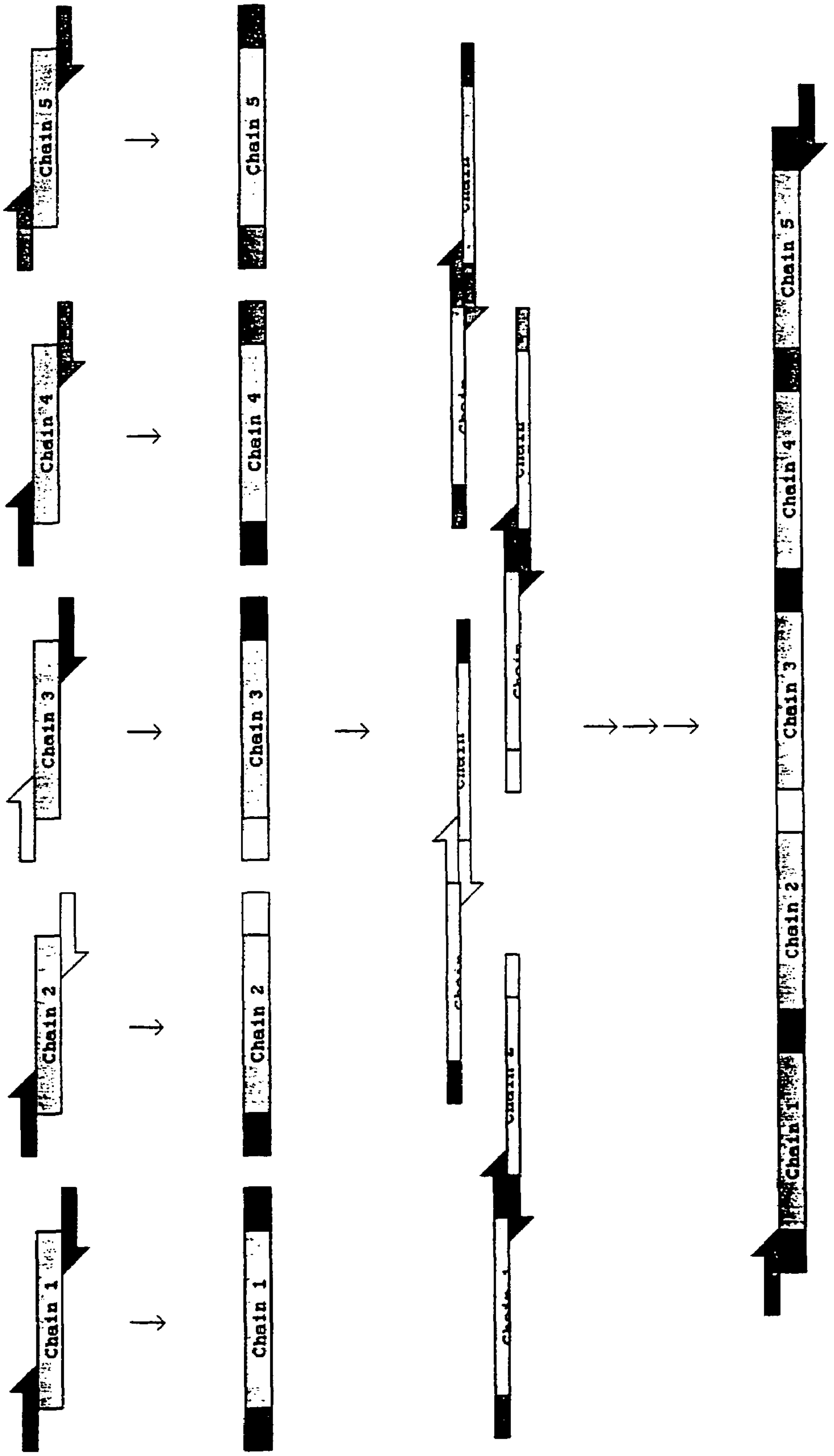

The following examples are given by way of illustration only in which the Figures referred to are as follows:

FIG. 1 shows a schematic representation of how the method of the invention may be used to introduce an insert into a vector, in which the insert is cleaved from the first nucleic acid molecule, associated with adapters and ligated thereto and then ligated into the vector;

FIG. 2 shows the production of a fragment chain using 8 "O" and "1" starting fragments with different overhangs (aaaaaaaaaa[SEQ ID NO:100], aaaaaaaaac[SEQ ID NO:54], aaaaaaaccg[SEQ ID NO:57], cccccccccgg[SEQ ID NO:59], cccccccccgcg[SEQ ID NO:56], cccccccccttt[SEQ ID NO:53], ggggggggaaa[SEQ ID NO:51], ggggggggaac [SEQ ID NO:52], ggggggggccg[SEQ ID NO:55], tttttttcgg [SEQ ID NO:60], tttttttgcg[SEQ ID NO:58], tttttttttt[SEQ ID NO:101]);

FIG. 3 shows the production of a 64 fragment chain in which 8 chains are produced comprising 8 fragments each, in which the termini of chains 1 and 2, and 2 and 3 etc. are complementary such that they may be ligated together (aaaaaaaaaa[SEQ ID NO:100], aaaaaaaaaaaa[SEQ ID NO:102], aaaggggggggaaa[SEQ ID NO:61], aacaaaaaaaaaa [SEQ ID NO:62], aacggggggggaaa[SEQ ID NO:103], cttc-cccccccccg[SEQ ID NO:104], cttttttttttcg[SEQ ID NO:105], ggggggggaaa[SEQ ID NO:51], gttcccccccccg[SEQ ID NO:65], gttttttttttcg[SEQ ID NO:66], tttcccccccccg[SEQ ID NO:63], tttttttttcg[SEQ ID NO:64]);

FIG. 4 shows 3 techniques for mixing "O", "1" fragments from a library of fragments ordered for each position, in which in A) appropriate fragments are selected by aspiration from appropriate wells, B) appropriate fragments are released from the library is wells and C) a flow cytometer is used to direct appropriate droplets to the mixing chamber;

FIG. 5 shows PCR amplification of signal chain 1-0-1-0-0 using SP6 and T7 primers. Lane 1: 1 μg of 1 kb DNA ladder (Gibco BRL), Lane 2: 10 μl of PCR amplified fragment chain DNA using SP6 and T7 primers. Lane 3: Same as lane 2 except for the use of SP6 and T7-Cy5 primers; and FIG. 6 shows the use of primer pairs during the process of amplification to join together fragment chains.

EXAMPLE 1

Cloning of an Insert into a Vector, for Example from PHIX174 into PUC19

A general procedure to be followed using IIS and IP enzymes to achieve cloning involves the use of a cloning vector which has the following characteristics:

1) A multiple cloning site located within a gene (lacZ, ccdB or other) that allows the detection of successful insertion.

2) The multiple cloning site contains two flanking HgaI sites that generates overhangs that differ from other HgaI generated overhangs elsewhere in the vector. The orientation of the HgaI sites ensures excision of its sites from the vector part during digestion. To minimize background due to undigested plasmids, several HgaI sites and other suitable restriction enzyme sites are included in the MCS. The restriction enzymes are chosen such that they cleave well in HgaI buffer and do not have other sites in the vector.

The donor plasmid is cut with the appropriate set of IIS and/or IP enzymes. Adapters are used to specify the fragment to be sub-cloned into the vector, by the use of appropriate single stranded regions on the adapters to the overhangs generated on the insert. This results in the molecule: vector-adapter 1-insert (e.g. PhiX174 gene)-adapter II-vector.

This method is illustrated for insertion of a PhiX174 insert into a vector, e.g. pUC19. An HgaI site in a pUC19 plasmid is chosen randomly to be our "polylinker" while different genes and gene combinations from the PhiX174 genome is used as "inserts".

Genomes are organized in PhiX174 as illustrated below which shows the position of genes A, B, C and E relative to one another:

```
---[--------------A--------------]------------------

--------------------[-----B-----]--------------------

---------------------------------[---C---]----------
```

-continued

```
-------------------------------------------[---E--]-

-1----2--3----4-----5---------------6---------7-8-----9
```

In the above, gene B is located inside gene A while gene C is slightly overlapping with gene A (by 3 base pairs). Gene D and K are located in the same area as gene C and E, but are not shown. This genome area contains 9 BbvI sites as shown on the bottom row, in which the overhang pairs that will be generated by cutting with BbvI are as follows with the base pair position indicated in brackets: 1-CAGC/GTCG (3798), 2-CTGC/GACG (4215), 3-ACGG/TGCC (4398), 3-GCAT/CGTA (4677), 5-CTAT/GATA (5049), 6-GAGA/CTCT (158), 7-GAGC/CTCG (547), 8-CAAC/GTTG (624), 9-CCAT/GGTA (892). The parts of the PhiX174 genome not shown contain 5 more BbvI sites: 10-TACC/ATGG (1488), 11-TACC/ATGG (1592), 12-CTAC/GATG (1639), 13-GCAC/CGTG (3294), 14-CTAA/GATT (3297). Of these only 12 give rise to non-identical overhangs whilst 2 result in identical overhangs.

When HgaI is used to cleave pUC19, 4 non-identical sites are cleaved, giving rise to 8 non-identical overhangs. These are: 1-CTGCC/GACGG (573), 2-TTCTC/AAGAG (1131), 3-CAAGG/GTTCC (1881), 4-AGACT/TCTGA (2459).

Method:

To sub-clone gene B from Bacteriophage PhiX174 into the designed vector, the following protocol is used:

1) 2 μg of PhiX174 DNA is digested with 2 U of BbvI (NEB) in 1× buffer 2 (NEB), water added to a volume of 20 μl, for 1 hr at 37° C. BbvI is then heat inactivated at 65° C. for 20 minutes.

2) 2 μg of vector (e.g. pUC19) is digested with 2 U HgaI (NEB) in 1× buffer 1 (NEB), water added to a volume of 20 μl, for 1 hr at 37° C. HgaI is then heat inactivated at 65° C. for 20 minutes.

3) The adapters are made in separate tubes by mixing two and two oligonucleotides (selected to obtain the desired product, ie. particular gene(s), in forward/reverse orientation) and allowing annealing.

4) 6 μl of the cleavage reaction of PhiX174 is mixed with 3 μl of the cleavage reaction of the vector and ligated in the presence of 5-50 pmol of each adaptor, 2-10 U/μl T4 DNA Ligase (NEB), 1× ligase buffer (NEB) and 5% Polyethylene glycol 8000, water added to a volume of 30 μl, at 25° C. for 1 hr.

5) Conventional methods are used to transform bacteria.

6) The colonies are then counted and some of them are then picked for further analysis (sequencing, and the like).

Materials:

Oligonucleotides used to address PhiX174 overhangs:

```
BbvI overhang 1a:
5'- CGA GCG CCT CCA GTG CAG CGG AG     [SEQ ID NO:3]

BbvI overhang 5a:
5'- TATC GCG CCT CCA GTG CAG CGG AG    [SEQ ID NO:4]

BbvI overhang 6b:
5'- CTCT GCG CCT CCA GTG CAG CGG AG    [SEQ ID NO:5]
```

-continued

```
BbvI overhang 6(delC):
5'- CTCT CTC CGC TGC ACT GGA GGC GC    [SEQ ID NO:6]

BbvI overhang 7a:
5'- CAAC GCG CCT CCA GTG CAG CGG AG    [SEQ ID NO:7]

BbvI overhang 9b:
5'- GGTA GCG CCT CCA GTG CAG CGG AG    [SEQ ID NO:8]
```

Oligonucleotides used to address pUC19 overhangs:

```
Cloning site 1a
5'- AAGAG CTC CGC TGC ACT GGA GGC GC   [SEQ ID NO:9]

Cloning site 1b
5'- CTCTT CTC CGC TGC ACT GGA GGC GC  [SEQ ID NO:10]
```

Two important advantages with this recombination-method over the classical Cohen-Boyer method should be noted. The procedure is very easy to perform. It involves only mixing and incubation steps before transformation. No PCR-amplifications or gel separations are required. The methods gives significant flexibility and allows complex recombinations to be made even with only two restriction enzymes.

EXAMPLE 2

Automation and Miniaturisation of Chain Synthesis

This method describes a rapid process for mixing appropriate “0” and “1” fragments with the correct overhangs to produce a particular string consisting of “0”'s and “1”'s.

Two libraries are produced, one with “0” fragments and one with “1” fragments. As mentioned in the description, these are generated with overhangs that can be ligated to corresponding overhangs for fragments at adjacent positions. These separate members are present in separate wells to form the library, such that position 1 fragments are present in well 1, position 2 fragments are present in well 2 and so forth. The two libraries thus provide the alternatives for each position. In order to generate the chain therefore it is only necessary to select the correct fragment “0” or “1” for position 1, and then position 2 etc. Since these fragments, as a consequence of their unique overhangs, may only hybridize to fragments for adjacent positions, it is necessary only to select the correct fragments, then mix and ligate those fragments simultaneously. Different ways of achieving this effect are shown in FIG. 4 which shows three different alternatives for mixing.

In FIG. 4A, e.g. to produce the chain 0-1-0-0-1, the apparatus is used to aspirate from the “0” library at positions 1, 3 and 4, and aspirate from the “1” library at position 2 and 5. The liquids that have been aspirated may then be mixed together with ligase and an appropriate buffer. In alternative B, each well in the library is connected with a tube/nozzle that may be closed/opened electronically. Liquid from the nozzles is directed into the ligation chamber together with ligase and an appropriate buffer. Different chains may be constructed by appropriately changing the pattern of nozzles which are opened/closed.

The procedure may also be miniaturised, e.g. using flow cytometry technology as illustrated in FIG. 4C. In this method, library components are stored in containers on top of the "writing-machine". Droplets from each container are then guided either to the waste or production well depending on the nature of the chain that is to be constructed. The guiding mechanism is as used in ordinary flow cytometers, ie. the droplets are charged when they leave the container and may be guided electronically in different directions.

EXAMPLE 3

Libraries Comprising Oligonucleotides for Use in the Invention

Conveniently, the cloning method may be performed using libraries containing oligonucleotides. For example a library may contain:

1. Oligonucleotides with a common portion and 5 bases at the 5' end which vary to provide all possible permutations, ie. 1024 variants.

2. Oligonucleotides with a common portion and 4 bases at the 5' end which vary to provide all possible permutations, ie. 256 variants.

3. Oligonucleotides with a common portion and 5 bases at the 3' end which vary to provide all possible permutations, ie. 1024 variants.

4. Oligonucleotides with a common portion and 6 bases at the 3' end which vary to provide all possible permutations, ie. 4096 variants.

In the above, the oligonucleotides are produced such that all "1" oligonucleotides are complementary to "2" oligonucleotides by virtue of the invariant bases, ie. to generate a double stranded molecule with variant 4/5 base overhangs. Similarly "3" and "4" oligonucleotides are complementary.

Oligonucleotides combined in this way (ie. with overhangs at either end of 4-6 bases may also be combined together with complementary double stranded oligonucleotides also generated by combining certain members of the library. In this way variable overhangs of different lengths may be created in the resultant molecule, e.g. a molecule with a 4 base overhang at both the 3' and 5' end.

Oligonucleotides may also be provided in the library which allow 5' and 3' adapters to be linked. Thus for example oligonucleotides having the following form may be provided:

5. 5'-AAAA-[compl]-FFFFF-3'

6. 5'-DDDDD-[compl]-FFFFF-3'

7. 5'-AAAA-[compl]-HHHHHH-3'

8. 5'-DDDDD-[compl]-HHHHHH-3'

9. 3'-[compl*]-5'

10. 5'-BBBB-[comp2]-3'

11. 5'-EEEEE-[comp2*]-3'

12. 5'-[comp3]-GGGGG-3'

13. 5'-[comp3*]-IIIII-3' in which "compx" refer to a region which is complementary to region "compx*", ie. "5", "6", "7" or "8" can bind to "9". Furthermore, "comp2" can bind to oligonucleotide 1 above, "comp2a" can bind to oligonucleotide 2, "comp3" can bind to oligonucleotide "4" and "comp3*" can bind to oligonucleotide "3". The bases denoted "A" bind to "B", ie. "7" and "10" can bind at their ends. Similarly "D" binds to "E", "F" binds to "G" and "H" binds to "I". (These bases when together may have a variable content, e.g. AAAA=GAGA and then BBBB=TCTC.)

By appropriate use of the linkers described above, 5' and 3' adapters may be combined. For example, oligonucleotide "2" with a particular 4 base 5' overhang may be bound through its complementary region to an oligonucleotide linker "11" which will then leave a "EEEEE" overlap. This may be bound to oligonucleotide "8" through the overlap which may itself bind oligonucleotide "9" through its complementary region. The overlap "HHHHHH" may be bound to oligonucleotide "13" which may attach an oligonucleotide "4" through binding to the complementary region. Thus various permutations may be made which result in various overlap lengths, e.g. any combination of 4, 5, or 6 base overlaps which may on the same or different strands.

EXAMPLE 4

Trimming Procedure for Generating Unique Overhangs

The system presented here makes it possible to perform a trimming procedure with seven different IIS enzymes that make 5' 4 base overhangs (FokI and Bst71I), 5' 5 base overhangs (HgaI), 3' 5 base overhangs (BplI and BaeI) and 3' 6 base overhangs (CjeI and HaeIV). If the oligonucleotide system presented here is combined with the basic oligonucleotide kit described in Example 3, all permutations of 3' 5 base and 6 base overhangs and all permutations of 5' 4 base and 5 base overhangs can be addressed for the trimming procedure.

In this Example, the location of the binding motifs of the initiation linkers is shown below:

```
                                            [SEQ ID NO:11]
FokI       ----------------------------GGATG----
Bst71I     --GCAGC------------------------------
HgaI       --------------------------------GACGC
BplI       -------------GAG-----CTC-------------
BaeI       ---------CYATG----CA-----------------
CjeI       -----------------CCA------GT---------
HaeIV      -------GAY-----RTC-------------------
Consensus  --GCAGCGACCATGAGTCCA-CTC--GTGGATGACGC
```

Initiation Linkers:

```
Initiation linkers:

X = 0:                                      [SEQ ID NO:12]
5' --GCAGCGACCATGAGTCCA-CTC--GTGGATGPPPPPP

                                            [SEQ ID NO:69]
3' --CGTCGCTGGTACTCAGGT-GAG--CACCTAC
```

-continued

```
X = 1:                                          [SEQ ID NO:13]
5' --GCAGCGACCATGAGTCCA-CTC--GTGGATG-PPPPPP

                                                [SEQ ID NO:70]
3' --CGTCGCTGGTACTCAGGT-GAG--CACCTAC-

X = 2:                                          [SEQ ID NO:14]
5' --GCAGCGACCATGAGTCCA-CTC--GTGGATG--PPPPPP

                                                [SEQ ID NO:71]
3' --CGTCGCTGGTACTCAGGT-GAG--CACCTAC--

X = 3:                                          [SEQ ID NO:15]
5' --GCAGCGACCATGAGTCCA-CTC--GTGGATG---PPPPPP

                                                [SEQ ID NO:72]
3' --CGTCGCTGGTACTCAGGT-GAG--CACCTAC---

X = 4:                                          [SEQ ID NO:16]
5' --GCAGCGACCATGAGTCCA-CTC--GTGGATGACGCPPPPPP

                                                [SEQ ID NO:73]
3' --CGTCGCTGGTACTCAGGT-GAG--CACCTACTGCG

X = 5:                                          [SEQ ID NO:17]
5' --GCAGCGACCATGAGTCCA-CTC--GTGGATGACGC-PPPPPP

                                                [SEQ ID NO:74]
3' --CGTCGCTGGTACTCAGGT-GAG--CACCTACTGCG-

X = 6:                                          [SEQ ID NO:18]
5' --GCAGCGACCATGAGTCCA-CTC--GTGGATGACGC--PPPPPP

                                                [SEQ ID NO:75]
3' --CGTCGCTGGTACTCAGGT-GAG--CACCTACTGCG--

X = 7:                                          [SEQ ID NO:19]
5' --GCAGCGACCATGAGTCCA-CTC--GTGGATGACGC---PPPPPP

                                                [SEQ ID NO:76]
3' --CGTCGCTGGTACTCAGGT-GAG--CACCTACTGCG---

X = 8:                                          [SEQ ID NO:20]
5' --GCAGCGACCATGAGTCCA-CTC--GTGGATGACGC----PPPPPP

                                                [SEQ ID NO:77]
3' --CGTCGCTGGTACTCAGGT-GAG--CACCTACTGCG----

X = 9:                                          [SEQ ID NO:21]
5' --GCAGCGACCATGAGTCCA-CTC--GTGGATGACGC-----PPPPPP

                                                [SEQ ID NO:78]
3' --CGTCGCTGGTACTCAGGT-GAG--CACCTACTGCG-----
```

The 6 base 3' overhang PPPPPP is a non-palindromic sequence that can be ligated with the complementary overhang QQQQQQ. The reason 10 different initiation linkers are needed is because BaeI cuts 10 bases away from its binding site. These linkers therefore allow a trimming procedure where BaeI "jumps" 10 bases for each trimming cycle. 10 different start positions will then be necessary to cover all possibilities. On the other side, HgaI cuts only 5 bases away, only necessitating 5 different start positions. This is the reason the binding site for HgaI is not present on X=0-X=3, above.

Propagation Linkers:

```
                                                [SEQ ID NO:79]
FokI:      5'------------------GGATG
           3'------------------CCTACNNNN

Bst71I:    5'------------------GCAGC
           3'------------------CGTCGNNNN

HgaI:      5'------------------GACGC
           3'------------------CTGCGNNNNN

SplI:      5'------------GAG-----CTCNNNN
           3'------------CTC-----GAG

BaeI:      5'------------CCATG----CANNNNN
           3'------------GGTAC----GT

HaeIV:     5'------------GAC-----GTCNNNNNNN
           3'------------CTG-----CTG

CjeI:      5'------------CCA------GTNNNNNN
           3'------------GGT------CA
```

Termination Linkers:

The adapters made with the basic oligonucleotides described earlier can be used as termination linkers. There is therefore no need for a separate set of termination linkers.

Method:

In this method a trimming reaction using Bst71I that will begin on a 3' 5 base overhang is shown. The target DNA is shown below in which the first overhang that will be generated is marked "*".

```
       ----*****-----------------------
3'CACTT----*****-----------------------
```

The first Bst71I overhang in the target DNA will be located 5-8 bases downstream of the overhang CACTT-3'. X must therefore be 3 (see the figure below). The following strategy can then be applied:

One linker is prepared that can address the 3' GTGAA overhang by annealing 4-3' 6 bases(QQQQQQ) with 3-3' 5 bases(GTAAA) in one tube:

```
            ------------------GTGAA -3'
3'- QQQQQQ------------------
```

The 3'-GAGTGC overhang is then ligated with the X=3 initiation linker and the GTGAA-3' overhang is ligated with the CACTT-3' overhang on the target DNA molecule:

```
                                                [SEQ ID NO:15]
5'--GCAGCGACCATGAGTCCA-CTC--GTGGATG---PPPPPP

                                                [SEQ ID NO:85]
3'--CGTCGCTGGTACTCAGGT-GAG--CACCTAC---QQQQQQ

             ------------------GTGAA------------3'
             ------------------CACTT------------5'
```

EXAMPLE 5

Removal of Intervening Sequences from Constructs

In some instances, constructs may be prepared which contain undesirable nucleic acid sequences between, e.g the insert sequence and the vector sequence. Strategies for removing the linker sequences should then be applied. Illustrated below are some possible strategies in which binding sites for restriction enzymes are provided in the adapter sequences. Cleavage with the restriction enzymes will then result in DNA ends that can be religated. The vector DNA is marked as . . . VVVVVVV while insert DNA is marked as IIIIII.

<u>Method 1</u>

```
Two IIS enzymes that generate 5'-4 base overhangs (BbsI and Esp3I)
5'..VVVVVVVVGAGC-GAGACG------GAAGAC--GACCIIIIIIIII  3'[SEQ ID NO:86]
3'  VVVVVVVVCTCG-CTCTGC------CTTCTG--CTCGIIIIIIIII..5'[SEQ ID NO:87]
```

<u>After cleavage with BbsI and Esp3I:</u>

```
..VVVVVVVV     + GAGC-GAGACG------GAAGAC-- [SEQ ID NO:88]+
  VVVVVVVVCTCG       -CTCTGC------CTTCTG--CTCG [SEQ ID NO:89]

GAGCIIIIIIIIII
    IIIIIIIIII..
```

<u>After ligation with T4 DNA ligase:</u>

```
GAGC-GAGACG------GAAGAC-- [SEQ ID NO:88]     +
    -CTCTGC------CTTCTG--CTCG [SEQ ID NO:89]

..VVVVVVVVGAGCIIIIIIIII [SEQ ID NO:90]
  VVVVVVVVCTCGIIIIIIIII.. [SEQ ID NO:91]
```

<u>Method 2</u>

```
One IIS enzyme that generates two 3' 3 base overhangs (BsaXI):
5'..VVVVVVVVGAG---------AC-----CTCC-------GAGIIIIIIIIII  3'[SEQ ID
NO:92]
3'  VVVVVVVVCTC---------TG-----GAGG-------CTCIIIIIIIIII..5'[SEQ ID
NO:93]
```

<u>After cleavage with BsaXI:</u>

```
..VVVVVVVVGAG +    ---------AC-----CTCC-------GAG [SEQ ID NO:94]
  VVVVVVVV      CTC---------TG-----GAGG------- [SEQ ID NO: 95]

+    IIIIIIIIII
  CTCIIIIIIIIII..
```

<u>After ligation with T4 DNA ligase:</u>

```
   ---------AC-----CTCC-------GAG [SEQ ID NO:94]+
CTC---------TG-----GAGG------- (SEQ ID NO: 95]

..VVVVVVVVGAGIIIIIIIIII
  VVVVVVVVCTCIIIIIIIIII..
```

<u>Method 3</u>

```
One IIS enzyme that generates blunt ends (MlyI):

5'..VVVVVVVV----------------GAGTC-----IIIIIIIIII  3'[SEQ ID NO:96]
3'  VVVVVVVV-----CTGAG----------------IIIIITIIII..5'[SEQ ID NO:96]
```

<u>After cleavage with MlyI:</u>

```
..VVVVVVVV + ----------------GAGTC----- [SEQ ID NO:97]+
  VVVVVVVV   -----CTGAG---------------- [SEQ ID NO:97]

IIIIIIIIII
IIIIIIIIII..
```

<u>After ligation with T4 DNA ligase:</u>

```
----------------GAGTC----- [SEQ ID NO:97]+
-----CTGAG---------------- [SEQ ID NO:97]

..VVVVVVVVIIIIIIIIII
..VVVVVVVVIIIIIIIIII..
```

EXAMPLE 6

Identifying Oligonucleotide Sets with 6 Base Pair Overhangs with Minimal Mis-Match Ligations In order to identify oligonucleotide sets with 6 base pair overhangs which are unlikely to form mis-match ligations with one another the following steps may be taken.

1. Create all 2048 overhang pairs of 6 bases.

2. Remove the 32 palindromic pairs.
This produces a final set of 2016 overhang pairs.

Part 1

1. Take a pair as pair #1 and select the next pair by executing section 1.

Section 1

Algorithm 1

Compute the (2016−n) tables of unweighted mismatch scores between the already chosen n pair(s) and all (2016−n) remaining pairs, and find among the latter the pair(s) for which the lowest score in the table is the highest (see below for details about score computation). If there is only one such pair, then select it. If there are several pairs, then compute the weighted mismatch scores of the overhang comparisons that gave the lowest unweighted score and find the pair(s) for which the lowest weighted score is the highest. If there is only one such pair, then select it. If there are several pairs, then redo the whole procedure using the second lowest unweighted score in the mismatch table, then the third lowest, and so on. If several pairs remain tied after all mismatch scores have been considered, keep them all.

Repeat algorithm 1 for each selected pair and iterate it over the desired number of positions to obtain the chain(s) of overhang pairs. This procedure generates a tree with an overhang pair on each branch. The lowest unweighted and weighted mismatch scores of the particular combination of pairs at each point are computed. A particular pathway is stopped (1) when the desired number of positions is reached, or (2) when the combination of pairs is one that has already been found earlier, or (3) when the lowest mismatch scores of that combination are lower than the lowest scores of the complete chain(s) already constructed. Point (3) ensures that each new complete chain always has lowest mismatch scores that are higher than or at least equal to those of the previously constructed chain(s). Note also that, as a result of this process, all pairs in a given chain are unique and all complete chains in the tree are unique. The whole process terminates when the last pathway to be explored stops. Keep the complete chain(s) whose lowest mismatch scores are the highest.

Repeat section 1 starting with each of the 2016 pairs as pair #1 to produce a set of 2016 overhang chains. Find the best chain(s) by applying algorithm 2

Algorithm 2

For all chains, compute the tables of unweighted mismatch scores between all the pairs that are present in the chain, and find the chain(s) for which the lowest score in the table is the highest (see below for details). If there is only one such chain, then select it. If there are several chains, then compute the weighted mismatch scores of the overhang comparisons that gave the lowest unweighted score and find the chain(s) for which the lowest weighted score is the highest. If there is only one such chain, then select it. If there are several chains, then redo the whole procedure using the second lowest unweighted score in the mismatch table, then the third lowest, and so on. If several chains remain tied after all mismatch scores have been considered, then keep all of them.

This allows the production of a set of one or more overhang chains.

Part 2

Take a chain and execute section 2.

Section 2

Algorithm 3

For that chain, find the overhang pair(s) that is(are) responsible for the lowest unweighted and weighted scores in the table of mismatch scores between all pairs in the chain. Then, create new chains by substituting that pair with all remaining overhang pairs that are not present in the original chain (if there are several pairs to be substituted, substitute one pair at a time) From the complete set of newly generated chains and the original chain, select one or more chains following algorithm 2. Here, including the original chain into algorithm 2 ensures that the selected chains always have a mismatch score that is higher than or at least equal to the score of the original chain. The improvement (if any) may involve the lowest or nth lowest unweighted score, or the corresponding weighted score.

Repeat algorithm 3 for each selected chain. This procedure generates a tree with a chain on each branch. Each new chain which is added to the tree has a mismatch score higher than or equal to the score of the chain found in the previous step. A particular pathway is stopped when the selected chain is one that has already been found earlier. This ensures that all chains in the tree are unique. The whole process terminates when the last pathway to be explored stops. Keep all the chains that are present in the tree.

Repeat section 2 (i.e., construct a tree) starting with each of the chains selected at the end of part 1.

From the whole set of chains present in all trees, select one or more chains following algorithm 2.

This produces a final set of one or more overhang chains.

Computation of Mismatch Scores

Unweighted Score

The unweighted score for a ligation between two 6-base overhangs is the number of mismatches observed, considering the triplets of the first 3 and the last 3 bases separately. For example, the score for the ligation AAAAAC/TTTGCA is 0-3 and the score for AAAAAC/TCAGGG is 2-2. All possible scores are ranked from highest to lowest according to the order below:

| | |
|---|---|
| highest: | 3-3 |
| | 3-2/2-3 |
| | 2-2 |
| | 3-1/1-3 |
| | 2-1/1-2 |
| | 1-1 |
| | 3-0/0-3 |
| | 2-0/0-2 |
| lowest: | 1-0/0-1 |

Weighted Score

The weighted score (WS) for a ligation is computed as follows:

$$WS = 6 - \sum_{i=1}^{6} BPS_i$$

where $BPS_i$ is the score for the particular base pair at site i and is given in the table below:

| | | | |
|---|---|---|---|
| AA = 1.0 | CA = 0.6 | GA = 1.0 | TA = 0.0 |
| AC = 0.6 | CC = 1.0 | GC = 0.0 | TC = 0.6 |
| AG = 1.0 | CG = 0.0 | GG = 0.9 | TG = 0.2 |
| AT = 0.0 | CT = 0.6 | GT = 0.2 | TT = 0.6 |

For the perfect match between an overhang and its complement, WS=6.

Comparison Among Pairs and Construction of Tables of Scores

Finding the Next Overhang Pair

To select the next overhang pair, tables of mismatch scores between the pairs selected at previous positions and all remaining pairs are computed. To construct such a table, all previously selected pairs are compared with the new pair and also every overhang is compared with itself. Thus, if n pairs have already been selected, the number of ligations considered for each table is 4n+2(n+1)=6n+2. When comparing two overhangs that are on the same DNA strand, one of them is reversed.

Let us consider the following example where pairs AAAAAC/TTTTTG (1A/1B) and AAACGT/TTTGCA (2A/2B) have been chosen previously and the new pair AGTCCC/TCAGGG (3A/3B) is tried at the next position:

The corresponding table is:

| Comparison | Overhang | Ligation | Unweighted Score | Weighted Score |
|---|---|---|---|---|
| 1 vs 1 | 1A | AAAAAC | 3-3 | 0.8 |
| | 1A | CAAAAA | | |
| | 1B | TTTTTG | 3-3 | 3.2 |
| | 1B | GTTTTT | | |
| 2 vs 2 | 2A | AAACGT | 2-2 | 2.8 |
| | 2A | TGCAAA | | |
| | 2B | TTTGCA | 2-2 | 4.4 |
| | 2B | ACGTTT | | |
| 3 vs 3 | 3A | AGTCCC | 2-2 | 3.6 |
| | 3A | CCCTGA | | |
| | 3B | TCAGGG | 2-2 | 3.6 |
| | 3D | GGGACT | | |
| 1 vs 3 | 1A | AAAAAC | 3-2 | 2.6 |
| | 3A | CCCTGA | | |
| | 1A | AAAAAC | 2-2 | 2.4 |
| | 3D | TCAGGG | | |
| | 1B | TTTTTG | 2-2 | 4.0 |
| | 3A | AGTCCC | | |
| | 1B | TTTTTG | 3-2 | 4.6 |
| | 3B | GGGACT | | |
| 2 vs 3 | 2A | AAACGT | 3-2 | 2.7 |
| | 3A | CCCTGA | | |
| | 2A | AAACGT | 2-2 | 3.3 |
| | 3D | TCAGGG | | |
| | 2B | TTTGCA | 2-2 | 3.6 |
| | 3A | AGTCCC | | |
| | 2B | TTTGCA | 3-2 | 3.4 |
| | 3B | GGGACT | | |

Here, the lowest score is 2-2; 2.4 given by the ligation between overhangs 1A and 3B.

Score Table for a Chain

To compute the table of mismatch scores for a chain, all overhang pairs contained in the chain are compared with each other and also every overhang is compared with itself. Thus, for a chain of p overhang pairs, the number of ligations considered is 4p(p−1)/2+2p=2(p2). As above, one of the two overhangs is reversed in the comparison when both are on the same DNA strand.

For example, let us consider the following 3-pair (i.e., 4-position) chain: AAAAAC/TTTTTG (1A/1B), AAACGT/TTTGCA (2A/2B), AGTCCC/TCAGGG (3A/3B) in which 1A is on one fragment, 1B and 2A are on a second fragment, 2B and 3A are on a third fragment and 3B is on a fourth fragment.

The corresponding table is:

| Comparison | Overhang | Ligation | Unweighted Score | Weighted Score |
|---|---|---|---|---|
| 1 vs 1 | 1A | AAAAAC | 3-3 | 0.8 |
| | 1A | CAAAAA | | |
| | 1B | TTTTTG | 3-3 | 3.2 |
| | 1B | GTTTTT | | |
| 2 vs 2 | 2A | AAACGT | 2-2 | 2.8 |
| | 2A | TGCAAA | | |
| | 2B | TTTGCA | 2-2 | 4.4 |
| | 2B | ACGTTT | | |
| 3 vs 3 | 3A | AGTCCC | 2-2 | 3.6 |
| | 3A | CCCTGA | | |
| | 3B | TCAGGG | 2-2 | 3.6 |
| | 3B | GGGACT | | |
| 1 vs 2 | 1A | AAAAAC | 2-3 | 1.8 |
| | 2A | TGCAAA | | |
| | 1A | AAAAAC | 0-3 | 3.8 |
| | 2B | TTTGCA | | |
| | 1B | TTTTTG | 0-3 | 5.0 |
| | 2A | AAACGT | | |
| | 1B | TTTTTG | 2-3 | 3.8 |
| | 2B | ACGTTT | | |
| 1 vs 3 | 1A | AAAAAC | 3-2 | 2.6 |
| | 3A | CCCTGA | | |
| | 1A | AAAAAC | 2-2 | 2.4 |
| | 3B | TCAGGG | | |
| | 1B | TTTTTG | 2-2 | 4.0 |
| | 3A | AGTCCC | | |
| | 1B | TTTTTG | 3-2 | 4.6 |
| | 3B | GGGACT | | |
| 2 vs 3 | 2A | AAACGT | 3-2 | 2.7 |
| | 3A | CCCTGA | | |
| | 2A | AAACGT | 2-2 | 3.3 |
| | 3B | TCAGGG | | |
| | 2B | TTTGCA | 2-2 | 3.6 |
| | 3A | AGTCCC | | |
| | 2B | TTTGCA | 3-2 | 3.4 |
| | 3B | GGGACT | | |

Here, the lowest score is 0-3; 3.8 given by the ligation between overhangs 1A and 2B.

Results Obtained:

Table of Breaking Points

PART 1

| # of positions | Unweighted score | Weighted score | # of equal chains |
|---|---|---|---|
| 3 | 3-3 | 1.6 | 48 |
| 4 | 2-2 | 4.0 | 48 |
| 9 | 2-2 | 2.5 | 12 |
| 10 | 3-1 | 3.2 | 12 |
| 14 | 3-1 | 2.4 | 6 |
| 15 | 2-1 | 4.6 | 6 |
| 33 | 2-1 | 3.0 | 12 |
| 34 | 3-0 | 4.6 | 12 |
| 90 | 3-0 | 3.1 | |

PART 2

| # of positions | Unweighted score | Weighted score | # of equal chains |
|---|---|---|---|
| 3 | 3-3 | 1.6 | 48 |
| 4 | 3-2 | 2.2 | 48 |
| 9 | 2-2 | 2.5 | 12 |
| 10 | 3-1 | 3.2 | 12 |
| 14 | 3-1 | 2.4 | 6 |
| 15 | 3-1 | 2.0 | 6 |
| 33 | 2-1 | 3.0 | 12 |
| 34 | 3-0 | 4.6 | 12 |
| 90 | | | |

It will be noted that the unweighted mis-match score (in which (9=3-3, 8=3-2, 7=2-2, 6=3-1, 5=2-1, 4=1-1, 3=3-0, 2=2-0, 1=1-0) reduces as the number of positions increases.

Samples of Chains Obtained at the End of Part 1 and at the End of Part 2

3 positions (this chain is obtained at the end of both parts):

AACTCC/TTGAGC
TCTCAC/AGAGTG 4 positions:

part 1

AATTGG/TTAACC
TGCCAC/ACGGTG
ATAGTC/TATCAG part 2

AATGGG/TTACCC
TCGGAC/AGCCTG
TTAACG/AATTGC 9 positions (this chain is obtained at the end of both parts):

| | | |
|---|---|---|
| AATCAC/TTAGTG | TACACG/ATGTGC | AGGCTG/TCCGAC |
| TGAGGG/ACTCCC | ACATTC/TGTAAG | TTTAGC/AAATCG |
| TCGGAT/AGCCTA | GGCTAG/CCGATC | |

10 positions (this chain is obtained at the end of both parts):

| | | |
|---|---|---|
| AAAACC/TTTTGG | AGGCTC/TCCGAG | TCGATA/AGCTAT |
| TTGGGG/AACCCC | GTCATG/CAGTAC | ATTCAG/TAAGTC |
| TCATAG/AGTATC | TGCAGT/ACGTCA | AGAGAT/TCTCTA |

14 positions (this chain is obtained at the end of both parts):

| | | |
|---|---|---|
| ACGTGC/TGCACG | GTTGGC/CAACCG | TCAGCC/AGTCGG |
| TATGAG/ATACTC | TTGCGG/AACGCC | AGAGGG/TCTCCC |

-continued

| | | |
|---|---|---|
| TGCACG/ACGTGC | AGTATC/TCATAG | CACCGC/GTGGCG |
| ATACAC/TATGTG | TGACTA/ACTGAT | |
| AACTTG/TTGAAC | ACTCCG/TGAGGC | |

15 positions:

part 1

| | | |
|---|---|---|
| AAAACC/TTTTGG | TGCAGT/ACGTCA | AAGTAA/TTCATT |
| TTGGGG/AACCCC | TCGATA/AGCTAT | CCGTCC/GGCAGG |
| TCATAG/AGTATC | ATTCAG/TAAGTC | TGTAAC/ACATTG |
| AGGCTC/TCCGAG | AGAGAT/TCTCTA | ACCGTG/TGGCAC |
| GTCATG/CAGTAC | TACTTC/ATGAAG | |

part 2

| | | |
|---|---|---|
| AAAACC/TTTTGG | TCTGCT/AGACGA | AAGTAA/TTCATT |
| TTGGGG/AACCCC | TCGATA/AGCTAT | CCGTCC/GGCAGG |
| TCATAG/AGTATC | ATTCAG/TAAGTC | TGTAAC/ACATTG |
| AGGCTC/TCCGAG | AGAGAT/TCTCTA | ACCGTG/TGGCAC |
| GACAAG/CTGTTC | TACTTC/ATGAAG | |

33 positions (this chain is obtained at the end of both parts):

| | | |
|---|---|---|
| AACTAG/TTGATC | GTAAGG/CATTCC | TCGCCT/AGCGGA |
| TGGAGC/ACCTCG | AAACTA/TTTGAT | TCTCGG/AGAGCC |
| TCAAAT/ACTTTA | CTCTCC/CAGAGG | ACCCCC/TGGGGG |
| CAGGCC/GTCCGG | ACAGCG/TGTCGC | TTTTCC/AAAAGC |
| TATCAC/ATAGTG | CACATC/GTGTAG | AAGTCA/TTCAGT |
| AGATTC/TCTAAG | TGTGTA/ACACAT | GTTCTC/CAAGAG |
| TTCCGT/AAGGCA | TAATGC/ATTACG | |
| CCCACG/GGGTGC | GGTAAG/CCATTC | |
| ATGCCG/TACGGC | AGTTAT/TCAATA | |
| TCCGTC/AGGCAG | CAACAG/GTTCTC | |
| CCACGC/GGTGCG | ATCGGC/TAGCCG | |
| ACTATG/TGATAC | AATGCT/TTACGA | |
| TTAGCA/AATCGT | TTGGAG/AACCTC | |

34 positions (this chain is obtained at the end of both parts):

| | | |
|---|---|---|
| AACTCT/TTGAGA | TTATTC/AATAAG | CCAATC/GGTTAG |
| TCGAAC/AGCTTG | CACAAG/GTGTTC | ACTTAT/TGAATA |
| CAGGGC/GTCCCG | TCCGAT/AGGCTA | AAAGAG/TTTCTC |
| TAAAGG/ATTTCC | AGTAGC/TCATCG | TTGATA/AACTAT |
| TGTGCG/ACACGC | CCGTCG/GGCAGC | AAGACC/TTCTGG |
| ATGTAG/TACATC | TCACTA/AGTGAT | CAATCC/GTTAGG |
| TTCCCC/AAGGGG | GTGACG/CACTGC | TCTCGC/AGAGCG |
| AATCTC/TTAGAG | TGAAAT/ACTTTA | AGGGGG/TCCCCC |
| TGGCGT/ACCGCA | AGCATG/TCGTAC | TGCCAG/ACGGTC |
| GGCTGC/CCGACG | ACCGTC/TGGCAG | TACTAC/ATGATG |
| TTTGAC/AAACTG | | |
| ACACCG/TGTGGC | | |
| TGAGGC/ACTCCG | | |

90 positions (this chain is obtained at the end of part 1):

| | | |
|---|---|---|
| AAAAAA/TTTTTT | TCTGGC/AGACCG | AAACGG/TTTGCC |
| CCGGCC/GGCCGG | ACGCAG/TGCGTC | TTTGCC/AAACGG |
| AGGTAG/TCCATC | TGCGTC/ACGCAG | AACCAA/TTGGTT |
| TCCATC/AGGTAG | AGTCAT/TCAGTA | CAAAAC/GTTTTG |
| ATCTGC/TAGACG | TCAGTA/AGTCAT | AAGGAA/TTCCTT |
| TAGACG/ATCTGC | CAGCCG/GTCGGC | CGCCGC/GCGGCG |
| ACTGTG/TGACAC | GTCGGC/CAGCCG | ACTGCG/TCACGC |
| TGACAC/ACTGTG | AATTTC/TTAAAG | TCACGC/AGTGCG |
| CATTAC/GTAATG | TTAAAG/AATTTC | ATTTTA/TAAAAT |
| ACCCCA/TGGGGT | CCAACG/GGTTGC | ATCCTA/TAGGAT |
| ATGGTA/TACCAT | GGTTGC/CCAACG | AGTATC/TCATAG |
| CGAAGC/GCTTCG | CACCAC/GTGGTG | TCATAG/AGTATC |
| ATTACC/TAATGG | AGAATA/TCTTAT | ATGTGG/TACACC |
| TAATGG/ATTACC | TCTTAT/AGAATA | TACACC/ATGTGG |
| CTCCTC/GAGGAG | ATCAAT/TAGTTA | ATGCAC/TACGTG |
| AGTTGA/TCAACT | TAGTTA/ATCAAT | TACGTG/ATGCAC |
| AATGCT/TTACGA | ACTTCA/TGAAGT | ACTAAC/TGATTG |
| TTACGA/AATGCT | AGCCCC/TCGGGG | TGATTG/ACTAAC |
| AAGCGC/TTCGCG | TCGGGG/AGCCCC | CAGTGC/GTCACG |
| TTCGCG/AAGCGC | ACCATG/TGGTAC | GTCACG/CAGTGC |
| CCCAAG/GGGTTC | TGGTAC/ACCATG | AATAAG/TTATTC |
| GGGTTC/CCCAAG | AGGGGA/TCCCCT | TTATTC/AATAAG |
| ACATCC/TGTAGG | CTAATC/GATTAG | AGATAT/TCTATA |
| TGTAGG/ACATCC | CGAGAG/GCTCTC | TCTATA/AGATAT |
| AACTTG/TTGAAC | GCTCTC/CGAGAG | AAGTCG/TTCAGC |
| TTGAAC/AACTTG | ACACGT/TGTGCA | TTCAGC/AAGTCG |
| ATAGAC/TATCTG | TGTGCA/ACACGT | AATCGA/TTAGCT |
| TATCTG/ATAGAC | CCTGTC/GGACAG | TTAGCT/AATCGA |

-continued

| | | |
|---|---|---|
| AGACCG/TCTGGC | GGACAG/CCTGTC | AGGCTC/TCCGAG |
| TCCGAG/AGGCTC | | |
| CGCGGC/GCCCCG | | |

EXAMPLE 7

Construction of a 5-Fragment Chain Encoding the Binary Sequence 1-0-1-0-0

This experiment demonstrates the construction of a specific 5 fragment chain using a set of four non-palindromic 5' 6 base overhang pairs. The set of four unique overhang pairs was found using a computer program as described in Example 6.

Based upon the overhang pairs, a set of five library components was made by annealing complementary oligonucleotides in separate tubes:

The library components (4 pmol each) were then mixed together and ligated using 100 U T4 DNA ligase (NEB) in 1× ligase buffer at 25° C. for 15 minutes. The ligase was then inactivated at 65° C. for 20 min.

5 μl of the ligation reaction (5 μl) was used as template in a PCR reaction (5 μl) containing 1× Thermopol buffer (NEB), 0.05 mM dNTPs, 0.4 μM T7 primer, 0.4 μM SP6 primer and 0.04 U/μl Vent polymerase (NEB). The PCR was hot started (95° C. for 3 minutes before addition of polymerase) and cycled 30 times; 95° C., 30 sec; 55° C., 30 sec; 76° C., 30 sec, using a PTC-200 thermo cycler (MJ Research). 10 μl of the PCR was analysed on a 1.5% agarose gel as shown in FIG. 5. The gel picture showed only one intense band corresponding to approximately 240 bp as expected (243 bp). The remaining PCR product was extracted twice with chloroform and precipitated using 71' ethanol and 0.1M NaAc. The DNA was dissolved in water and sequenced. The sequence confirmed that the expected signal chain (1-0-1-0-0) was generated.

```
signal 1:

5'-TAATACGACTCACTATACCACAAGTTTGTACAAAAAAGCAGGCTCTATTC-3'[SEQ ID NO:22]

and

5'-TAGGAAGAATAGAGCCTGCTTTTTTGTACAACTTGTGGTATAGTGAGTCGTATTA-3'[SEQ ID NO:23];

signal 2:

5'-TTCCTATGCAGTGGACCACTTGTACAAGAAAGCTGGGTTGCAGT-3'[SEQ ID NO:24]

and

5'-GCAACTACTGCAACCCAGCTTTCTTGTACAAAGTGGTCCACTGCA-3'[SEQ ID NO:25];

signal 3:

5'-AGTTGCTTGACGCCACAAGTTTGTACAAAAAAGCAGGCTTTGACG-3'[SEQ ID NO:26]

and

5'-CGACATCGTCAAAGCCTGCTTTTTTGTACAAACTTGTGGCGTCAA-3'[SEQ ID NO:27];

signal 4:

5'-ATGTCGAAGGGCGGACCACTTTGTACAAGAAAGCTGGGTAAGGGC-3'[SEQ ID NO:28]

and

5'-GACAGGGCCCTTACCCAGCTTTCTTGTACAAAGTGGTCCGCCCTT-3'[SEQ ID NO:29];

signal 5:

5'-CCTGTCATGTGGACCACTTTGTACAAGAAAGCTGGGTTTCTATAGTGTCACCTAAATC-3'[SEQ ID NO:30]

and

5'-GATTTAGGTGACACTATAGAAACCCAGCTTTCTTGTACAAAGTGGTCCACAT-3'[SEQ ID NO:31];

T7: 5'-TAATACGACTCACTATACCA-3'[SEQ ID NO:32];

T7-CyS primer: 5'-TAATACGACTCACTATA-3'[SEQ ID NO:33];

and

SP6 primer: 3'-AAGATATCACAGTGGATTTAG-5'[SEQ ID NO:34].
```

EXAMPLE 8

Construction of a 5×5 Fragment Chain Encoding the Binary Sequence Using One Ligation Cycle Followed by One Pct Cycle or by Two Ligation Cycles This experiment demonstrates the use of complementary primer pairs to link fragment chains together as an alternative to the ligation strategy demonstrated in the previous example.

In this experiment 5 fragments chains with 5 positions (fragments or bits) each are ligated separately in ligation cycle 1 as demonstrated earlier (Example 7). The 5 fragment chains are then amplified with 5 different primer pairs (pair 1 is used to amplify chain 1, pair 2 is used to amplify chain 2, etc). The second primer in primer pair 1 is complementary to the first primer in prime pair 2, the second primer in primer pair 2 is complementary to the first primer in primer pair 3, and so on.

A small aliquot is then taken from each of the 5 PCR reactions and a new PCR reactions is performed with primers that are specific to the end of signal chain 1 and 5. The method is illustrated in FIG. 6.

Materials:

Oligonucleotides are selected which bind to the fragment chain and also serve as primers. Thus for example, for adjacent chains may be bound using for example the following primer pairs:

```
fragment chain 2 terminal (with bound primer):
5'TTCTATAGTGTCACCTAAATC3'[SEQ ID NO:35]

3'AAGATATCACAGTGGATTTAGCCTACCAGTACATCCAACGGCAACT5'
[SEQ ID NO: 36]

fragment chain 3 terminal (with bound primer):
5'GTCATGTAGGTTGCCGTTGATCCATCCTAATACGACTCACTATAGCA3'
[SEQ ID NO:37]

                                3'ATTATGCTGAGTGATATCGT5'
[SEQ ID NO:38]
```

The above exemplified primer regions are complementary and may thus be bound together.

As an alternative to this method, two ligation cycles may be used in which 5 fragment chains (generated by ligation), are ligated together. Thus, several construction cycles to build up long signal chains. After the initial ligation in the first ligation cycle the 5 fragment chains are then amplified with primers containing a FokI site. The primers are appropriately selected such that digestion with FokI will then make non-palindromic overhangs in the end of each fragment chain in which the overhang generated in fragment chain 1 is able to ligate with the first overhang generated in fragment chain 2, the second overhang generated in fragment chain 2 is able to ligate with the first overhang generated in fragment chain 3, and so on. The 5 fragment chains can thereby be ligated together in a controlled manner to generate a final chain with 25 fragments (bits).

If we want to construct fragment chains with 100 or 500 fragments we can repeat this procedure 1 or 2 more times. The polymerase capacity will, however, be a limiting factor regarding how many ligation cycles it is possible to perform. Other strategies will therefore need to be employed to construct even longer chains.

EXAMPLE 9

Cloning of an Insert from PHIX174 into PUC1 with a Trimmed Gene A

This experiment demonstrates the "trimming" strategy for elimination of unwanted flanking sequences. Another important aspect of this experiment is that we demonstrate that it is possible to link a 5' and 3' overhang together with a single stranded oligonucleotide alone. It should also be noted that the inserts are cloned into two different IIS sites, thereby eliminating the problem with insert concatemerisation.

In this method, Gene A from PhiX174 is cloned into a pUC-19 vector. PhiX174 is prepared by cleavage with BbvI, resulting in 15 fragments flanked by different non-palindromic 5' 4 bases overhangs, as described in more detail in Example 1. The two overhangs adjacent to Gene A is then addressed with "initiation linkers" containing a BplI site, while the rest of the fragments is allowed to religate. T4 DNA ligase, BplI, a "propagation linker" containing a BplI site, and two "termination adaptors" addressed to the first and last five bases of Gene A respectively are used. The solution is incubated at 37° C. thereby allowing the trimming reaction to succeed until terminated when the five first and last bases in Gene A are reached.

The pUC-19 vector is prepared by cleavage with HgaI and BsaI. The overhang generated by HgaI cleavage are described in Example 1. Cleavage with BsaI results in 4 non-identical cleavages giving rise to 8 non-identical overhangs, e.g. site 1-GCCA/CGGT (1600).

Gene A has the following sequence at its first and last five bases (marked by underlining).

```
                                    [SEQ ID NO:80]
5'...GCTGGAGGCCTCCACTATGAAATCGCGTAGAG...
                                    [SEQ ID NO:98]
3'...CGACCTCCGGAGGTGATACTTTAGCGCATC.....

                                    [SEQ ID NO:81]
 .....CTGGCGGAAAATGAGAAAATTCGACCTA...3'
                                    [SEQ ID NO:99]
 ...ACGACCGCCTTTTACTCTTTTAAGCTGG.....5'
```

When terminating the trimming procedure at the underlined sequences it is possible to clone Gene A without any unwanted flanking base pairs. The 3' 5 base overhangs generated by BplI correspond to the marked base pairs.

The overhang pair generated by HgaI and BsaI in pUC19 that is used as a cloning site for the gene A from PhiX174 is TTCTC/CGGT.

Method:

This is as described in Example 1 except that PUC19 is cut with both HgaI (NEB 4, 37° C.) and thereafter with BsaI (NEB 4, 50° C.)

Materials:

Initiation linker 1 (s):

5' ATT CGG TCG AGA TGC TCT CA 3' [SEQ ID NO:39]

Initiator linker 1 (as):

5' CGA CTG AGA GCA TCT CGA CCG AAT 3' [SEQ ID NO:40]

Initiation linker 2 (s):

5' GCG TTA CTG AGC GTA GCT CTG 3' [SEQ ID NO:41]

Initiator linker 2 (as):

5' CTC TCA GAG CTA CGC TCA GTA ACG C 3' [SEQ ID NO:42]

Propagation linker (s):

5' TGC TGC AGG AGC GAA TCT CNN NNN 3' [SEQ ID NO:43]

Propagation linker (as):

5' GAG ATT CGC TCC TGC AGC A 3' [SEQ ID NO:44]

Labeling linker 2 (s):

5' CTC TTG CTA TAG TGA GTC GTA TTA 3' [SEQ ID NO:45]

Labeling linker 2 (as):

5' TAA TAC GAC TCA CTA TAG CA 3' [SEQ ID NO:46]

Termination linker 1 (s):

5' AAG AGC TCA GGT CAT TGA CGT AGC TAT GAA 3' [SEQ ID NO:47]

Termination linker 1/2 (as):

5' AGC TAC GTC AAT GAC CTG AG 3' [SEQ ID NO:48]

Termination linker I (short version):

5' AAG AGA TGA A 3' [SEQ ID NO:49]

Termination linker 2 (s):

5' ACC GCT CAG GTC ATT GAC GTA GCT TCA TT 3' [SEQ ID NO:50]

Termination linker 2 (short version):

5' ACC GTC ATT 3'

The efficiency of the trimming reaction may be accessed as follows. Overhang 6) is addressed with a γ-$^{32}$P labelled adaptor. The trimming reaction is then allowed to start from overhang 1). Aliquots are taken out at regularly time intervals and the size distribution of the DNA fragments is then analysed on gel.

SEQUENCE LISTING

<160> NUMBER OF SEQ ID NOS: 105

<210> SEQ ID NO 1
<211> LENGTH: 11
<212> TYPE: DNA
<213> ORGANISM: Artificial Sequence
<220> FEATURE:
<223> OTHER INFORMATION: Adapter
<220> FEATURE:
<221> NAME/KEY: misc_feature -continued
<222> LOCATION: (8)..(9)
<223> OTHER INFORMATION: N is any nucleotide.

<400> SEQUENCE: 1
ggcccccnna a 11

<210> SEQ ID NO 2
<211> LENGTH: 11
<212> TYPE: DNA
<213> ORGANISM: Artificial Sequence
<220> FEATURE:
<223> OTHER INFORMATION: Adapter
<220> FEATURE:
<221> NAME/KEY: misc_feature
<222> LOCATION: (7)..(9)
<223> OTHER INFORMATION: N is any nucleotide.

<400> SEQUENCE: 2
ggggccnnnc t 11

<210> SEQ ID NO 3
<211> LENGTH: 23
<212> TYPE: DNA
<213> ORGANISM: Artificial Sequence
<220> FEATURE:
<223> OTHER INFORMATION: BbvI overhang

<400> SEQUENCE: 3
cgagcgcctc cagtgcagcg gag 23

<210> SEQ ID NO 4
<211> LENGTH: 24
<212> TYPE: DNA
<213> ORGANISM: Artificial Sequence
<220> FEATURE:
<223> OTHER INFORMATION: BbvI overhang

<400> SEQUENCE: 4
tatcgcgcct ccagtgcagc ggag 24

<210> SEQ ID NO 5
<211> LENGTH: 24
<212> TYPE: DNA
<213> ORGANISM: Artificial Sequence
<220> FEATURE:
<223> OTHER INFORMATION: BbvI overhang

<400> SEQUENCE: 5
ctctgcgcct ccagtgcagc ggag 24

<210> SEQ ID NO 6
<211> LENGTH: 24
<212> TYPE: DNA
<213> ORGANISM: Artificial Sequence
<220> FEATURE:
<223> OTHER INFORMATION: BbvI overhang 6 (delC)

<400> SEQUENCE: 6
ctctctccgc tgcactggag gcgc 24

<210> SEQ ID NO 7
<211> LENGTH: 24
<212> TYPE: DNA
<213> ORGANISM: Artificial Sequence
<220> FEATURE:
<223> OTHER INFORMATION: BbvI overhang 7a -continued

<400> SEQUENCE: 7
caacgcgcct ccagtgcagc ggag 24

<210> SEQ ID NO 8
<211> LENGTH: 24
<212> TYPE: DNA
<213> ORGANISM: Artificial Sequence
<220> FEATURE:
<223> OTHER INFORMATION: BbvI overhang 9b

<400> SEQUENCE: 8
ggtagcgcct ccagtgcagc ggag 24

<210> SEQ ID NO 9
<211> LENGTH: 25
<212> TYPE: DNA
<213> ORGANISM: Artificial Sequence
<220> FEATURE:
<223> OTHER INFORMATION: Cloning site 1a

<400> SEQUENCE: 9
aagagctccg ctgcactgga ggcgc 25

<210> SEQ ID NO 10
<211> LENGTH: 25
<212> TYPE: DNA
<213> ORGANISM: Artificial Sequence
<220> FEATURE:
<223> OTHER INFORMATION: Cloning site 1b

<400> SEQUENCE: 10
ctcttctccg ctgcactgga ggcgc 25

<210> SEQ ID NO 11
<211> LENGTH: 35
<212> TYPE: DNA
<213> ORGANISM: Artificial Sequence
<220> FEATURE:
<223> OTHER INFORMATION: Consensus binding motifs of the initiation
linkers
<220> FEATURE:
<221> NAME/KEY: misc_feature
<222> LOCATION: (19)..(24)
<223> OTHER INFORMATION: N is any nucleotide.

<400> SEQUENCE: 11
gcagcgacca tgagtccanc tcnngtggat gacgc 35

<210> SEQ ID NO 12
<211> LENGTH: 37
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (19)..(37)
<223> OTHER INFORMATION: N is any nucleotide with the proviso that the
DNA sequence from 32 to 37 is not palindromic.

<400> SEQUENCE: 12
gcagcgacca tgagtccanc tcnngtggat gnnnnnn 37

<210> SEQ ID NO 13
<211> LENGTH: 38
<212> TYPE: DNA
<213> ORGANISM: Artificial Sequence -continued

```
<220> FEATURE:
<223> OTHER INFORMATION: Initiation linker
<220> FEATURE:
<221> NAME/KEY: misc_feature
<222> LOCATION: (19)..(38)
<223> OTHER INFORMATION: N is any nucleotide with the proviso that the
      DNA sequence from 33 to 38 is not palindromic.

<400> SEQUENCE: 13

gcagcgacca tgagtccanc tcnngtggat gnnnnnnn                          38


<210> SEQ ID NO 14
<211> LENGTH: 39
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (19)..(39)
<223> OTHER INFORMATION: N is any nucleotide with the proviso that the
      DNA sequence from 34 to 39 is not palindromic.

<400> SEQUENCE: 14

gcagcgacca tgagtccanc tcnngtggat gnnnnnnnn                         39


<210> SEQ ID NO 15
<211> LENGTH: 40
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (19)..(40)
<223> OTHER INFORMATION: N is any nucleotide with the proviso that the
      DNA sequence from 35 to 40  is not palindromic.

<400> SEQUENCE: 15

gcagcgacca tgagtccanc tcnngtggat gnnnnnnnnn                        40


<210> SEQ ID NO 16
<211> LENGTH: 41
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (19)..(41)
<223> OTHER INFORMATION: N is any nucleotide with the proviso that the
      DNA sequence from 36 to 41 is not palindromic.

<400> SEQUENCE: 16

gcagcgacca tgagtccanc tcnngtggat gacgcnnnnn n                      41


<210> SEQ ID NO 17
<211> LENGTH: 42
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (19)..(42)
<223> OTHER INFORMATION: N is any nucleotide with the proviso that the
      DNA sequence from 37 to 42 is not palindromic.

<400> SEQUENCE: 17

gcagcgacca tgagtccanc tcnngtggat gacgcnnnnn nn                     42
```

<210> SEQ ID NO 18
<211> LENGTH: 43
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (19)..(43)
<223> OTHER INFORMATION: N is any nucleotide with the proviso that the
DNA sequence from 38 to 43 is not palindromic.

<400> SEQUENCE: 18
gcagcgacca tgagtccanc tcnngtggat gacgcnnnnn nnn 43

<210> SEQ ID NO 19
<211> LENGTH: 44
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (19)..(44)
<223> OTHER INFORMATION: N is any nucleotide with the proviso that the
DNA sequence from 39 to 44 is not palindromic.

<400> SEQUENCE: 19
gcagcgacca tgagtccanc tcnngtggat gacgcnnnnn nnnn 44

<210> SEQ ID NO 20
<211> LENGTH: 45
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (19)..(45)
<223> OTHER INFORMATION: N is any nucleotide with the proviso that the
DNA sequence from 40 to 45 is not palindromic.

<400> SEQUENCE: 20
gcagcgacca tgagtccanc tcnngtggat gacgcnnnnn nnnnn 45

<210> SEQ ID NO 21
<211> LENGTH: 46
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (19)..(46)
<223> OTHER INFORMATION: N is any nucleotide with the proviso that the
DNA sequence from 41 to 46 is not palindromic.

<400> SEQUENCE: 21
gcagcgacca tgagtccanc tcnngtggat gacgcnnnnn nnnnnn 46

<210> SEQ ID NO 22
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 22

-continued taatacgact cactatacca caagtttgta caaaaaagca ggctctattc 50

<210> SEQ ID NO 23
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 23
taggaagaat agagcctgct tttttgtaca aacttgtggt atagtgagtc gtatta 56

<210> SEQ ID NO 24
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 24
ttcctatgca gtggaccact ttgtacaaga aagctgggtt gcagt 45

<210> SEQ ID NO 25
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 25
gcaactactg caacccagct ttcttgtaca aagtggtcca ctgca 45

<210> SEQ ID NO 26
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 26
agttgcttga cgccacaagt ttgtacaaaa aagcaggctt tgacg 45

<210> SEQ ID NO 27
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 27
cgacatcgtc aaagcctgct tttttgtaca aacttgtggc gtcaa 45

<210> SEQ ID NO 28
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 28
atgtcgaagg gcggaccact ttgtacaaga aagctgggta agggc 45

<210> SEQ ID NO 29
<211> LENGTH: 45
<212> TYPE: DNA
<213> ORGANISM: Artificial Sequence -continued
<220> FEATURE:
<223> OTHER INFORMATION: Synthetic oligonucleotide

<400> SEQUENCE: 29
gacagggccc ttacccagct ttcttgtaca aagtggtccg ccctt 45

<210> SEQ ID NO 30
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 30
cctgtcatgt ggaccacttt gtacaagaaa gctgggtttc tatagtgtca cctaaatc 58

<210> SEQ ID NO 31
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 31
gatttaggtg acactataga aacccagctt tcttgtacaa agtggtccac at 52

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
taatacgact cactatacca 20

<210> SEQ ID NO 33
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 33
taatacgact cactata 17

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34
aagatatcac agtggattta g 21

<210> SEQ ID NO 35
<211> LENGTH: 21
<212> TYPE: DNA
<213> ORGANISM: Artificial Sequence
<220> FEATURE:
<223> OTHER INFORMATION: Fragment chain 2 terminal

<400> SEQUENCE: 35
ttctatagtg tcacctaaat c 21

-continued

<210> SEQ ID NO 36
<211> LENGTH: 46
<212> TYPE: DNA
<213> ORGANISM: Artificial Sequence
<220> FEATURE:
<223> OTHER INFORMATION: Primer

<400> SEQUENCE: 36
tcaacggcaa cctacatgac catccgattt aggtgacact atagaa 46

<210> SEQ ID NO 37
<211> LENGTH: 47
<212> TYPE: DNA
<213> ORGANISM: Artificial Sequence
<220> FEATURE:
<223> OTHER INFORMATION: Primer

<400> SEQUENCE: 37
gtcatgtagg ttgccgttga tccatcctaa tacgactcac tatagca 47

<210> SEQ ID NO 38
<211> LENGTH: 20
<212> TYPE: DNA
<213> ORGANISM: Artificial Sequence
<220> FEATURE:
<223> OTHER INFORMATION: Fragment chain 3 terminal

<400> SEQUENCE: 38
tgctatagtg agtcgtatta 20

<210> SEQ ID NO 39
<211> LENGTH: 20
<212> TYPE: DNA
<213> ORGANISM: Artificial Sequence
<220> FEATURE:
<223> OTHER INFORMATION: Initiation linker 1 (s)

<400> SEQUENCE: 39
attcggtcga gatgctctca 20

<210> SEQ ID NO 40
<211> LENGTH: 24
<212> TYPE: DNA
<213> ORGANISM: Artificial Sequence
<220> FEATURE:
<223> OTHER INFORMATION: Initiation linker 1 (as)

<400> SEQUENCE: 40
cgactgagag catctcgacc gaat 24

<210> SEQ ID NO 41
<211> LENGTH: 21
<212> TYPE: DNA
<213> ORGANISM: Artificial Sequence
<220> FEATURE:
<223> OTHER INFORMATION: Initiation linker 2

<400> SEQUENCE: 41
gcgttactga gcgtagctct g 21

<210> SEQ ID NO 42
<211> LENGTH: 25
<212> TYPE: DNA
<213> ORGANISM: Artificial Sequence
<220> FEATURE:
<223> OTHER INFORMATION: Initiation linker 2 (as)

-continued

<400> SEQUENCE: 42
ctctcagagc tacgctcagt aacgc 25

<210> SEQ ID NO 43
<211> LENGTH: 24
<212> TYPE: DNA
<213> ORGANISM: Artificial Sequence
<220> FEATURE:
<223> OTHER INFORMATION: Propagation linker (s)
<220> FEATURE:
<221> NAME/KEY: misc_feature
<222> LOCATION: (20)..(24)
<223> OTHER INFORMATION: N is any nucleotide.

<400> SEQUENCE: 43
tgctgcagga gcgaatctcn nnnn 24

<210> SEQ ID NO 44
<211> LENGTH: 19
<212> TYPE: DNA
<213> ORGANISM: Artificial Sequence
<220> FEATURE:
<223> OTHER INFORMATION: Propagation linker (as)

<400> SEQUENCE: 44
gagattcgct cctgcagca 19

<210> SEQ ID NO 45
<211> LENGTH: 24
<212> TYPE: DNA
<213> ORGANISM: Artificial Sequence
<220> FEATURE:
<223> OTHER INFORMATION: Labeling linker 2 (s)

<400> SEQUENCE: 45
ctcttgctat agtgagtcgt atta 24

<210> SEQ ID NO 46
<211> LENGTH: 20
<212> TYPE: DNA
<213> ORGANISM: Artificial Sequence
<220> FEATURE:
<223> OTHER INFORMATION: Labeling linker 2 (as)

<400> SEQUENCE: 46
taatacgact cactatagca 20

<210> SEQ ID NO 47
<211> LENGTH: 30
<212> TYPE: DNA
<213> ORGANISM: Artificial Sequence
<220> FEATURE:
<223> OTHER INFORMATION: Termination linker 1 (s)

<400> SEQUENCE: 47
aagagctcag gtcattgacg tagctatgaa 30

<210> SEQ ID NO 48
<211> LENGTH: 20
<212> TYPE: DNA
<213> ORGANISM: Artificial Sequence
<220> FEATURE:
<223> OTHER INFORMATION: Termination linker 1/2 (as)

<400> SEQUENCE: 48
agctacgtca atgacctgag                                              20

<210> SEQ ID NO 49
<211> LENGTH: 10
<212> TYPE: DNA
<213> ORGANISM: Artificial Sequence
<220> FEATURE:
<223> OTHER INFORMATION: Termination linker 1 (short version)

<400> SEQUENCE: 49
aagagatgaa                                                         10

<210> SEQ ID NO 50
<211> LENGTH: 29
<212> TYPE: DNA
<213> ORGANISM: Artificial Sequence
<220> FEATURE:
<223> OTHER INFORMATION: Termination linker 2 (s)

<400> SEQUENCE: 50
accgctcagg tcattgacgt agcttcatt                                    29

<210> SEQ ID NO 51
<211> LENGTH: 11
<212> TYPE: DNA
<213> ORGANISM: Artificial Sequence
<220> FEATURE:
<223> OTHER INFORMATION: 0 starting fragment, position 1

<400> SEQUENCE: 51
ggggggggaa a                                                       11

<210> SEQ ID NO 52
<211> LENGTH: 11
<212> TYPE: DNA
<213> ORGANISM: Artificial Sequence
<220> FEATURE:
<223> OTHER INFORMATION: 0 starting fragment, position 2

<400> SEQUENCE: 52
ggggggggaa c                                                       11

<210> SEQ ID NO 53
<211> LENGTH: 12
<212> TYPE: DNA
<213> ORGANISM: Artificial Sequence
<220> FEATURE:
<223> OTHER INFORMATION: 0 starting fragment, position 2

<400> SEQUENCE: 53
ccccccccct tt                                                      12

<210> SEQ ID NO 54
<211> LENGTH: 10
<212> TYPE: DNA
<213> ORGANISM: Artificial Sequence
<220> FEATURE:
<223> OTHER INFORMATION: 1 starting fragment, postion 2

<400> SEQUENCE: 54
aaaaaaaaac                                                         10

<210> SEQ ID NO 55
<211> LENGTH: 11
<212> TYPE: DNA
<213> ORGANISM: Artificial Sequence -continued
<220> FEATURE:
<223> OTHER INFORMATION: 0 starting fragment, postion 7

<400> SEQUENCE: 55
ggggggggcc g 11

<210> SEQ ID NO 56
<211> LENGTH: 12
<212> TYPE: DNA
<213> ORGANISM: Artificial Sequence
<220> FEATURE:
<223> OTHER INFORMATION: 0 starting fragment, postion 7

<400> SEQUENCE: 56 ccccccccg cg 12

<210> SEQ ID NO 57
<211> LENGTH: 10
<212> TYPE: DNA
<213> ORGANISM: Artificial Sequence
<220> FEATURE:
<223> OTHER INFORMATION: 1 starting fragment, postion 7

<400> SEQUENCE: 57
aaaaaaaccg 10

<210> SEQ ID NO 58
<211> LENGTH: 11
<212> TYPE: DNA
<213> ORGANISM: Artificial Sequence
<220> FEATURE:
<223> OTHER INFORMATION: 1 starting fragment, postion 7

<400> SEQUENCE: 58
ttttttttgc g 11

<210> SEQ ID NO 59
<211> LENGTH: 12
<212> TYPE: DNA
<213> ORGANISM: Artificial Sequence
<220> FEATURE:
<223> OTHER INFORMATION: 0 starting fragment, postion 8

<400> SEQUENCE: 59
cccccccccc gg 12

<210> SEQ ID NO 60
<211> LENGTH: 11
<212> TYPE: DNA
<213> ORGANISM: Artificial Sequence
<220> FEATURE:
<223> OTHER INFORMATION: 1 starting fragment, postion 8

<400> SEQUENCE: 60
ttttttttcg g 11

<210> SEQ ID NO 61
<211> LENGTH: 14
<212> TYPE: DNA
<213> ORGANISM: Artificial Sequence
<220> FEATURE:
<223> OTHER INFORMATION: Fragment 0, position 1.2

<400> SEQUENCE: 61
aaaggggggg gaaa 14

-continued

<210> SEQ ID NO 62
<211> LENGTH: 13
<212> TYPE: DNA
<213> ORGANISM: Artificial Sequence
<220> FEATURE:
<223> OTHER INFORMATION: Fragment 1, position 1.3

<400> SEQUENCE: 62
aacaaaaaaa aaa 13

<210> SEQ ID NO 63
<211> LENGTH: 14
<212> TYPE: DNA
<213> ORGANISM: Artificial Sequence
<220> FEATURE:
<223> OTHER INFORMATION: Fragment 0, position 8.1

<400> SEQUENCE: 63
tttccccccc cccg 14

<210> SEQ ID NO 64
<211> LENGTH: 13
<212> TYPE: DNA
<213> ORGANISM: Artificial Sequence
<220> FEATURE:
<223> OTHER INFORMATION: Fragment 1, position 8.1

<400> SEQUENCE: 64
tttttttttt tcg 13

<210> SEQ ID NO 65
<211> LENGTH: 14
<212> TYPE: DNA
<213> ORGANISM: Artificial Sequence
<220> FEATURE:
<223> OTHER INFORMATION: Fragment 0, position 8.2

<400> SEQUENCE: 65
gttccccccc cccg 14

<210> SEQ ID NO 66
<211> LENGTH: 13
<212> TYPE: DNA
<213> ORGANISM: Artificial Sequence
<220> FEATURE:
<223> OTHER INFORMATION: Fragment 1, position 8.2

<400> SEQUENCE: 66
gttttttttt tcg 13

<210> SEQ ID NO 67
<211> LENGTH: 14
<212> TYPE: DNA
<213> ORGANISM: Artificial Sequence
<220> FEATURE:
<223> OTHER INFORMATION: Fragment 0, position 8.3

<400> SEQUENCE: 67
cttccccccc cccg 14

<210> SEQ ID NO 68
<211> LENGTH: 13
<212> TYPE: DNA
<213> ORGANISM: Artificial Sequence
<220> FEATURE:
<223> OTHER INFORMATION: Fragment 1, position 8.3

```
<400> SEQUENCE: 68

cttttttttt tcg                                                            13

<210> SEQ ID NO 69
<211> LENGTH: 31
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (8)..(13)
<223> OTHER INFORMATION: N is any nucleotide.

<400> SEQUENCE: 69

catccacnng agntggactc atggtcgctg c                                        31

<210> SEQ ID NO 70
<211> LENGTH: 32
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (1)..(14)
<223> OTHER INFORMATION: N is any nucleotide.

<400> SEQUENCE: 70

ncatccacnn gagntggact catggtcgct gc                                       32

<210> SEQ ID NO 71
<211> LENGTH: 33
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (1)..(15)
<223> OTHER INFORMATION: N is any nucleotide.

<400> SEQUENCE: 71

nncatccacn ngagntggac tcatggtcgc tgc                                      33

<210> SEQ ID NO 72
<211> LENGTH: 34
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (1)..(16)
<223> OTHER INFORMATION: N is any nucleotide.

<400> SEQUENCE: 72

nnncatccac nngagntgga ctcatggtcg ctgc                                     34

<210> SEQ ID NO 73
<211> LENGTH: 35
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (12)..(17)
```

-continued

<223> OTHER INFORMATION: N is any nucleotide.

<400> SEQUENCE: 73
gcgtcatcca cnngagntgg actcatggtc gctgc 35

<210> SEQ ID NO 74
<211> LENGTH: 36
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (1)..(18)
<223> OTHER INFORMATION: N is any nucleotide.

<400> SEQUENCE: 74
ngcgtcatcc acnngagntg gactcatggt cgctgc 36

<210> SEQ ID NO 75
<211> LENGTH: 37
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (1)..(19)
<223> OTHER INFORMATION: N is any nucleotide.

<400> SEQUENCE: 75
nngcgtcatc cacnngagnt ggactcatgg tcgctgc 37

<210> SEQ ID NO 76
<211> LENGTH: 38
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (1)..(20)
<223> OTHER INFORMATION: N is any nucleotide.

<400> SEQUENCE: 76
nnngcgtcat ccacnngagn tggactcatg gtcgctgc 38

<210> SEQ ID NO 77
<211> LENGTH: 39
<212> TYPE: DNA
<213> ORGANISM: Artificial Sequence
<220> FEATURE:
<223> OTHER INFORMATION: Initiation linker
<220> FEATURE:
<221> NAME/KEY: misc_feature
<222> LOCATION: (1)..(21)
<223> OTHER INFORMATION: N is any nucleotide.

<400> SEQUENCE: 77
nnnngcgtca tccacnngag ntggactcat ggtcgctgc 39

<210> SEQ ID NO 78
<211> LENGTH: 40
<212> TYPE: DNA
<213> ORGANISM: Artificial Sequence
<220> FEATURE:
<223> OTHER INFORMATION: Initiation linker
<220> FEATURE:
<221> NAME/KEY: misc_feature -continued
<222> LOCATION: (1)..(22)
<223> OTHER INFORMATION: N is any nucleotide.

<400> SEQUENCE: 78
nnnnngcgtc atccacnnga gntggactca tggtcgctgc 40

<210> SEQ ID NO 79
<211> LENGTH: 10
<212> TYPE: DNA
<213> ORGANISM: Artificial Sequence
<220> FEATURE:
<223> OTHER INFORMATION: Propagation linker HgaI
<220> FEATURE:
<221> NAME/KEY: misc_feature
<222> LOCATION: (1)..(5)
<223> OTHER INFORMATION: N is any nucleotide.

<400> SEQUENCE: 79 nnnnngcgtc 10

<210> SEQ ID NO 80
<211> LENGTH: 32
<212> TYPE: DNA
<213> ORGANISM: Artificial Sequence
<220> FEATURE:
<223> OTHER INFORMATION: Gene A from PHIX174

<400> SEQUENCE: 80
gctggaggcc tccactatga aatcgcgtag ag 32

<210> SEQ ID NO 81
<211> LENGTH: 28
<212> TYPE: DNA
<213> ORGANISM: Artificial Sequence
<220> FEATURE:
<223> OTHER INFORMATION: Gene A from PHIX174

<400> SEQUENCE: 81
ctggcggaaa atgagaaaat tcgaccta 28

<210> SEQ ID NO 82
<211> LENGTH: 13
<212> TYPE: DNA
<213> ORGANISM: Artificial Sequence
<220> FEATURE:
<223> OTHER INFORMATION: Recognition motif of the N-terminal part of the hsdS subunit of StyR 1241
<220> FEATURE:
<221> NAME/KEY: misc_feature
<222> LOCATION: (4)..(9)
<223> OTHER INFORMATION: N is any nucleotide.

<400> SEQUENCE: 82
gaannnnnnr tcg 13

<210> SEQ ID NO 83
<211> LENGTH: 14
<212> TYPE: DNA
<213> ORGANISM: Artificial Sequence
<220> FEATURE:
<223> OTHER INFORMATION: Recognition motif of the C-terminal part of the hsdS subunit of StyR 1241
<220> FEATURE:
<221> NAME/KEY: misc_feature
<222> LOCATION: (4)..(10)
<223> OTHER INFORMATION: N is any nucleotide.

<400> SEQUENCE: 83

-continued

```
tcannnnnnn rttc                                                     14


<210> SEQ ID NO 84
<211> LENGTH: 13
<212> TYPE: DNA
<213> ORGANISM: Artificial Sequence
<220> FEATURE:
<223> OTHER INFORMATION: Recognition motif of a new enzyme made by
      merging the N- and C-terminal parts of the hsdS subunit of StyR
      1241
<220> FEATURE:
<221> NAME/KEY: misc_feature
<222> LOCATION: (4)..(9)
<223> OTHER INFORMATION: N is any nucleotide.

<400> SEQUENCE: 84

gaannnnnnr ttc                                                      13


<210> SEQ ID NO 85
<211> LENGTH: 40
<212> TYPE: DNA
<213> ORGANISM: Artificial Sequence
<220> FEATURE:
<223> OTHER INFORMATION: Ligated initiation linker
<220> FEATURE:
<221> NAME/KEY: misc_feature
<222> LOCATION: (1)..(22)
<223> OTHER INFORMATION: N is any nucleotide with the proviso that the
      sequence from 1 to 6 is complemantary to the sequence from 40 to
      35 of SEQ ID NO: 15
      .

<400> SEQUENCE: 85

nnnnnnnnnc atccacnnga gntggactca tggtcgctgc                         40


<210> SEQ ID NO 86
<211> LENGTH: 47
<212> TYPE: DNA
<213> ORGANISM: Artificial Sequence
<220> FEATURE:
<223> OTHER INFORMATION: An example of sequences that generate 5'-4 base
      overhangs by BbsI and Esp3I
<220> FEATURE:
<221> NAME/KEY: misc_feature
<222> LOCATION: (1)..(47)
<223> OTHER INFORMATION: N is any nucleotide.

<400> SEQUENCE: 86

nnnnnnnnga gcngagacgn nnnnngaaga cnngagcnnn nnnnnnn                 47


<210> SEQ ID NO 87
<211> LENGTH: 47
<212> TYPE: DNA
<213> ORGANISM: Artificial Sequence
<220> FEATURE:
<223> OTHER INFORMATION: An example of sequences that generate 5'-4 base
      overhangs by BbsI and Esp3I
<220> FEATURE:
<221> NAME/KEY: misc_feature
<222> LOCATION: (1)..(47)
<223> OTHER INFORMATION: N is any nucleotide.

<400> SEQUENCE: 87

nnnnnnnnnn gctcnngtct tcnnnnnncg tctcngctcn nnnnnnn                 47


<210> SEQ ID NO 88
<211> LENGTH: 29
<212> TYPE: DNA
<213> ORGANISM: Artificial Sequence
<220> FEATURE:
```

-continued

<223> OTHER INFORMATION: An example of 5'-4 base overhangs generated by
      BbsI and Esp3I cleavage
<220> FEATURE:
<221> NAME/KEY: misc_feature
<222> LOCATION: (5)..(25)
<223> OTHER INFORMATION: N is any nucleotide.

<400> SEQUENCE: 88
gagcngagac gnnnnnngaa gacnngagc 29

<210> SEQ ID NO 89
<211> LENGTH: 25
<212> TYPE: DNA
<213> ORGANISM: Artificial Sequence
<220> FEATURE:
<223> OTHER INFORMATION: An example of 5'-4 base overhangs generated by
      BbsI and Esp3I cleavage
<220> FEATURE:
<221> NAME/KEY: misc_feature
<222> LOCATION: (5)..(25)
<223> OTHER INFORMATION: N is any nucleotide.

<400> SEQUENCE: 89
gctcnngtct tcnnnnnncg tctcn 25

<210> SEQ ID NO 90
<211> LENGTH: 22
<212> TYPE: DNA
<213> ORGANISM: Artificial Sequence
<220> FEATURE:
<223> OTHER INFORMATION: An example of ligation products between 5'-4
      base overhangs generated by BbsI and Esp3I cleavage
<220> FEATURE:
<221> NAME/KEY: misc_feature
<222> LOCATION: (1)..(22)
<223> OTHER INFORMATION: N is any nucleotide.

<400> SEQUENCE: 90
nnnnnnnnga gcnnnnnnnn nn 22

<210> SEQ ID NO 91
<211> LENGTH: 22
<212> TYPE: DNA
<213> ORGANISM: Artificial Sequence
<220> FEATURE:
<223> OTHER INFORMATION: An example of ligation products between 5'-4
      base overhangs generated by BbsI and Esp3I cleavage
<220> FEATURE:
<221> NAME/KEY: misc_feature
<222> LOCATION: (1)..(22)
<223> OTHER INFORMATION: N is any nucleotide.

<400> SEQUENCE: 91
nnnnnnnnnn gctcnnnnnn nn 22

<210> SEQ ID NO 92
<211> LENGTH: 51
<212> TYPE: DNA
<213> ORGANISM: Artificial Sequence
<220> FEATURE:
<223> OTHER INFORMATION: An example of sequences that generate two 3' 3
      base overhangs by BsaXI
<220> FEATURE:
<221> NAME/KEY: misc_feature
<222> LOCATION: (1)..(51)
<223> OTHER INFORMATION: N is any nucleotide.

<400> SEQUENCE: 92
nnnnnnnnga gnnnnnnnnn acnnnnnctc cnnnnnnnga gnnnnnnnnn n 51

-continued

<210> SEQ ID NO 93
<211> LENGTH: 51
<212> TYPE: DNA
<213> ORGANISM: Artificial Sequence
<220> FEATURE:
<223> OTHER INFORMATION: An example of sequences that generate two 3' 3 base overhangs by BsaXI
<220> FEATURE:
<221> NAME/KEY: misc_feature
<222> LOCATION: (1)..(51)
<223> OTHER INFORMATION: N is any nucleotide.

<400> SEQUENCE: 93
nnnnnnnnnn ctcnnnnnnn ggagnnnnng tnnnnnnnnn ctcnnnnnnn n 51

<210> SEQ ID NO 94
<211> LENGTH: 30
<212> TYPE: DNA
<213> ORGANISM: Artificial Sequence
<220> FEATURE:
<223> OTHER INFORMATION: An example of 3' 3 base overhangs generated by BsaXI cleavage
<220> FEATURE:
<221> NAME/KEY: misc_feature
<222> LOCATION: (1)..(27)
<223> OTHER INFORMATION: N is any nucleotide.

<400> SEQUENCE: 94
nnnnnnnnna cnnnnnctcc nnnnnnngag 30

<210> SEQ ID NO 95
<211> LENGTH: 30
<212> TYPE: DNA
<213> ORGANISM: Artificial Sequence
<220> FEATURE:
<223> OTHER INFORMATION: An example of 3' 3 base overhangs generated by BsaXI cleavage
<220> FEATURE:
<221> NAME/KEY: misc_feature
<222> LOCATION: (1)..(27)
<223> OTHER INFORMATION: N is any nucleotide.

<400> SEQUENCE: 95
nnnnnnngga gnnnnngtnn nnnnnnnctc 30

<210> SEQ ID NO 96
<211> LENGTH: 44
<212> TYPE: DNA
<213> ORGANISM: Artificial Sequence
<220> FEATURE:
<223> OTHER INFORMATION: An example of sequences that generated blunt ends by MlyI
<220> FEATURE:
<221> NAME/KEY: misc_feature
<222> LOCATION: (1)..(44)
<223> OTHER INFORMATION: N is any nucleotide.

<400> SEQUENCE: 96
nnnnnnnnnn nnnnnnnnnn nnnngagtcn nnnnnnnnnn nnnn 44

<210> SEQ ID NO 97
<211> LENGTH: 26
<212> TYPE: DNA
<213> ORGANISM: Artificial Sequence
<220> FEATURE:
<223> OTHER INFORMATION: An example of 3' 3 base overhangs generated by MlyI cleavage
<220> FEATURE:
<221> NAME/KEY: misc_feature
<222> LOCATION: (1)..(26)

-continued

<223> OTHER INFORMATION: N is any nucleotide.

<400> SEQUENCE: 97
nnnnnnnnnn nnnnnngagt cnnnnn 26

<210> SEQ ID NO 98
<211> LENGTH: 30
<212> TYPE: DNA
<213> ORGANISM: Artificial Sequence
<220> FEATURE:
<223> OTHER INFORMATION: Gene A from PHIX174

<400> SEQUENCE: 98
ctacgcgatt tcatagtgga ggcctccagc 30

<210> SEQ ID NO 99
<211> LENGTH: 28
<212> TYPE: DNA
<213> ORGANISM: Artificial Sequence
<220> FEATURE:
<223> OTHER INFORMATION: Gene A from PHIX174

<400> SEQUENCE: 99
ggtcgaattt tctcattttc cgccagca 28

<210> SEQ ID NO 100
<211> LENGTH: 10
<212> TYPE: DNA
<213> ORGANISM: Artificial Sequence
<220> FEATURE:
<223> OTHER INFORMATION: 1 starting fragment, position 1

<400> SEQUENCE: 100
aaaaaaaaaa 10

<210> SEQ ID NO 101
<211> LENGTH: 11
<212> TYPE: DNA
<213> ORGANISM: Artificial Sequence
<220> FEATURE:
<223> OTHER INFORMATION: 1 starting fragment, position 2

<400> SEQUENCE: 101
tttttttttt t 11

<210> SEQ ID NO 102
<211> LENGTH: 13
<212> TYPE: DNA
<213> ORGANISM: Artificial Sequence
<220> FEATURE:
<223> OTHER INFORMATION: Fragment 1, position 1.2

<400> SEQUENCE: 102
aaaaaaaaaa aaa 13

<210> SEQ ID NO 103
<211> LENGTH: 14
<212> TYPE: DNA
<213> ORGANISM: Artificial Sequence
<220> FEATURE:
<223> OTHER INFORMATION: Fragment 0, position 1.3

<400> SEQUENCE: 103
aacggggggg gaaa 14

-continued

```
<210> SEQ ID NO 104
<211> LENGTH: 14
<212> TYPE: DNA
<213> ORGANISM: Artificial Sequence
<220> FEATURE:
<223> OTHER INFORMATION: Fragment 0, position 8.3

<400> SEQUENCE: 104

cttcccccc cccg                                                          14


<210> SEQ ID NO 105
<211> LENGTH: 13
<212> TYPE: DNA
<213> ORGANISM: Artificial Sequence
<220> FEATURE:
<223> OTHER INFORMATION: Fragment 1, position 8.3

<400> SEQUENCE: 105

cttttttttt tcg                                                          13
```

The invention claimed is:

1. A method for synthesizing a double stranded nucleic acid molecule that contains information that represents computer-readable binary code, comprising at least the steps of:

i) hybridizing together a plurality of double-stranded nucleic acid fragments, each fragment consisting of between 8 and 25 bases and comprising at least one sequence of between 4 and 10 bases that represent a unit of the binary code, and each fragment comprising at least one single stranded region that is capable of hybridizing to at least one other fragment; and ii) optionally ligating the hybridized fragments;

to produce a double stranded nucleic acid molecule comprising a series of binary code units.

2. A method according to claim 1, wherein at least 10 double stranded nucleic acid fragments are hybridized together in step (i), to produce a double-stranded nucleic acid molecule comprising 10 fragments.

3. A method according to claim 1, wherein a plurality of double stranded nucleic acid molecules comprising a series of double-stranded nucleic acid fragments are synthesized and linked together.

4. A method of identifying at least one binary code unit contained within a double stranded nucleic acid molecule produced according to claim 1, comprising the steps of:

i) binding a labelled probe that is specific to at least one code unit to the unit; and ii) detecting the label associated with the bound probe, thereby detecting the presence of the binary code unit to which the probe binds.

* * * * *